United States Patent
Leung et al.

(10) Patent No.: US 12,201,400 B2
(45) Date of Patent: Jan. 21, 2025

(54) RELEASABLE PORTABLE IMAGING DEVICE FOR MULTISPECTRAL MOBILE TISSUE ASSESSMENT VIA DETERMINING DRIVING INTENSITY CORRECTION FOR LEDS

(71) Applicant: MIMOSA Diagnostics Inc., Toronto (CA)

(72) Inventors: General Leung, Toronto (CA); Yip Wing Wong, Toronto (CA); Dragos Ioan Duta, Toronto (CA); Nathan Swift, Toronto (CA); Armin Gurdic, Vancouver (CA)

(73) Assignee: MIMOSA Diagnostics Inc., Toronto (CA)

( * ) Notice: Subject to any disclaimer, the term of this patent is extended or adjusted under 35 U.S.C. 154(b) by 0 days.

(21) Appl. No.: 18/115,075

(22) Filed: Feb. 28, 2023

(65) Prior Publication Data

US 2023/0277064 A1    Sep. 7, 2023

Related U.S. Application Data

(60) Provisional application No. 63/315,493, filed on Mar. 1, 2022.

(51) Int. Cl.
*A61B 5/00*    (2006.01)
*A61B 90/00*    (2016.01)
(Continued)

(52) U.S. Cl.
CPC .......... *A61B 5/0077* (2013.01); *A61B 5/0037* (2013.01); *A61B 5/6898* (2013.01);
(Continued)

(58) Field of Classification Search
CPC ... A61B 5/0077; A61B 5/0037; A61B 5/6898; A61B 5/743; A61B 2090/061;
(Continued)

(56) References Cited

U.S. PATENT DOCUMENTS 6,640,130 B1    10/2003    Freeman et al.
6,810,279 B2    10/2004    Mansfield et al.
(Continued)

FOREIGN PATENT DOCUMENTS

CN            107515045 A        12/2017
DE      102016001513 A1 *    2/2016    ......... A61B 1/00009
(Continued)

*Primary Examiner* — Serkan Akar
(74) *Attorney, Agent, or Firm* — SMART & BIGGAR LP; Tonino Rosario Orsi

(57) ABSTRACT

A method for positioning a portable multispectral imaging device within a target distance range relative to a surface for imaging a region of interest (ROI) of the surface. The method generally involves determining a distance between the portable multispectral imaging device and the ROI of the surface determining whether the distance is within the target distance range generating a signal indicating to a user that the portable multispectral imaging device is not within the target distance range and providing instructions to the user to guide that the user for repositioning the portable multispectral imaging device; and triggering an image capturing sequence when the portable multispectral imaging device is within the target distance range. A method for calibrating a light source unit of the portable multispectral imaging device and a portable multispectral imaging device are also described.

10 Claims, 16 Drawing Sheets

(51) Int. Cl.
*G01S 17/08* (2006.01)
*H02J 7/00* (2006.01)
*H04N 23/10* (2023.01)
*H04N 23/51* (2023.01)
*H04N 23/56* (2023.01)
*H04N 23/60* (2023.01)
*H04N 23/74* (2023.01)
*G03B 15/06* (2021.01)

(52) U.S. Cl.
CPC .............. *A61B 5/743* (2013.01); *G01S 17/08* (2013.01); *H04N 23/10* (2023.01); *H04N 23/51* (2023.01); *H04N 23/56* (2023.01); *H04N 23/64* (2023.01); *H04N 23/74* (2023.01); *A61B 2090/061* (2016.02); *A61B 2560/0214* (2013.01); *A61B 2560/0223* (2013.01); *A61B 2560/0252* (2013.01); *A61B 2562/185* (2013.01); *G03B 15/06* (2013.01); *H02J 7/0048* (2020.01); *H02J 7/007182* (2020.01)

(58) Field of Classification Search
CPC .... A61B 2560/0214; A61B 2560/0223; A61B 2560/0252; A61B 2562/185; A61B 5/4842; A61B 5/0075; A61B 5/015; A61B 5/445; G01S 17/08; H04N 23/10; H04N 23/51; H04N 23/56; H04N 23/64; H04N 23/74; G03B 15/06; H02J 7/0048; H02J 7/007182
See application file for complete search history.

(56) References Cited

U.S. PATENT DOCUMENTS

| | | |
|---|---|---|
| 7,729,747 B2 | 6/2010 | Stranc et al. |
| 8,060,188 B2 | 11/2011 | Stranc et al. |
| 8,175,688 B2 | 5/2012 | Lewis et al. |
| 8,224,425 B2 | 7/2012 | Freeman et al. |
| 8,320,996 B2 | 11/2012 | Panasyuk et al. |
| 8,374,682 B2 | 2/2013 | Freeman et al. |
| 8,792,098 B2 | 7/2014 | Dewald et al. |
| 8,892,192 B2 | 11/2014 | Cuccia et al. |
| 8,971,984 B2 | 3/2015 | Freeman et al. |
| 9,480,424 B2 | 11/2016 | Darty et al. |
| 9,526,427 B2 | 12/2016 | Darty et al. |
| 9,841,322 B1 * | 12/2017 | Kemeny ................. G01J 3/108 |
| 9,968,285 B2 | 5/2018 | Valsan et al. |
| 10,278,636 B2 | 5/2019 | Li et al. |
| 10,952,616 B2 * | 3/2021 | Watanabe .......... G01N 21/4795 |
| 2007/0024946 A1 | 2/2007 | Panasyuk et al. |
| 2014/0176757 A1 * | 6/2014 | Rivard ..................... G06T 7/90 |
| | | 348/E9.051 |
| 2014/0253735 A1 | 9/2014 | Fox et al. |
| 2014/0293091 A1 | 10/2014 | Rhoads et al. |
| 2016/0022181 A1 * | 1/2016 | Valsan ................. A61B 5/0261 |
| | | 600/323 |
| 2016/0157725 A1 | 6/2016 | Munoz |
| 2017/0124709 A1 | 5/2017 | Rithe et al. |
| 2018/0106676 A1 | 4/2018 | Jang et al. |
| 2018/0160953 A1 | 6/2018 | Valsan et al. |
| 2018/0198993 A1 | 7/2018 | Barnes et al. |
| 2018/0295296 A1 | 10/2018 | Huang |
| 2018/0328855 A1 | 11/2018 | Kido |
| 2019/0065845 A1 | 2/2019 | Xu |
| 2019/0090751 A1 | 3/2019 | Hwang et al. |
| 2019/0216326 A1 | 7/2019 | Cross et al. |
| 2020/0121245 A1 * | 4/2020 | Barclay ................ A61B 5/1077 |
| 2023/0181042 A1 * | 6/2023 | Fan ...................... A61B 5/4842 |
| | | 424/78.06 |

FOREIGN PATENT DOCUMENTS

| | | | | |
|---|---|---|---|---|
| DE | 102016001513 B4 * | 2/2024 | ......... | A61B 1/00009 |
| WO | 2018035612 A1 | 3/2018 | | |
| WO | 2018160963 A1 | 9/2018 | | |
| WO | 2018211482 A1 | 11/2018 | | |
| WO | 2019003245 A1 | 1/2019 | | |
| WO | 2019054958 A2 | 3/2019 | | |
| WO | 2020148726 A1 | 7/2020 | | |

* cited by examiner

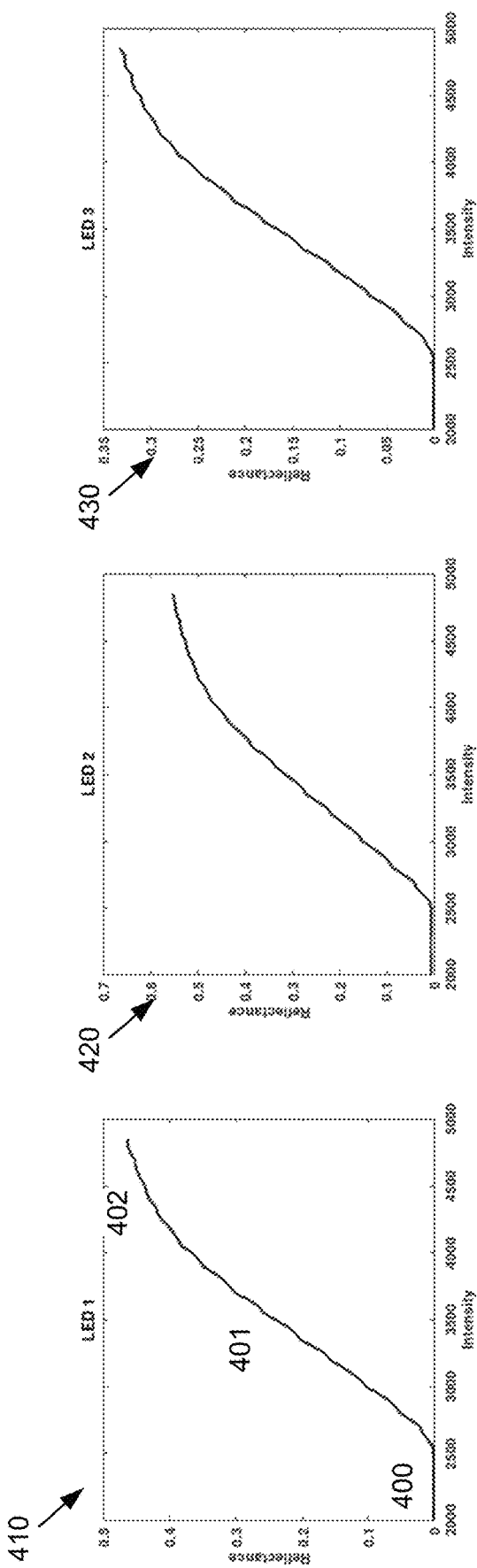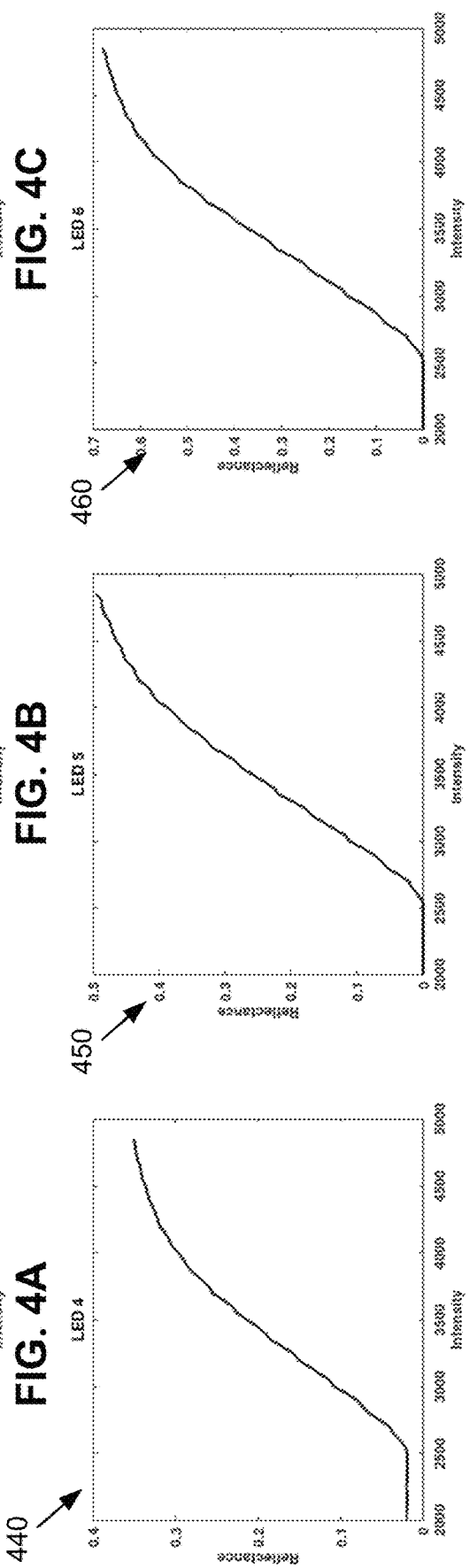

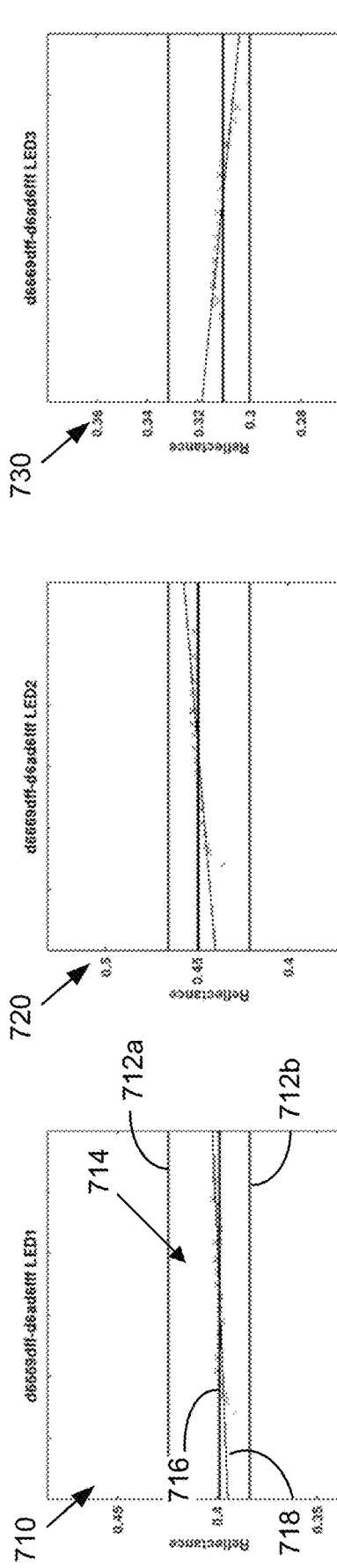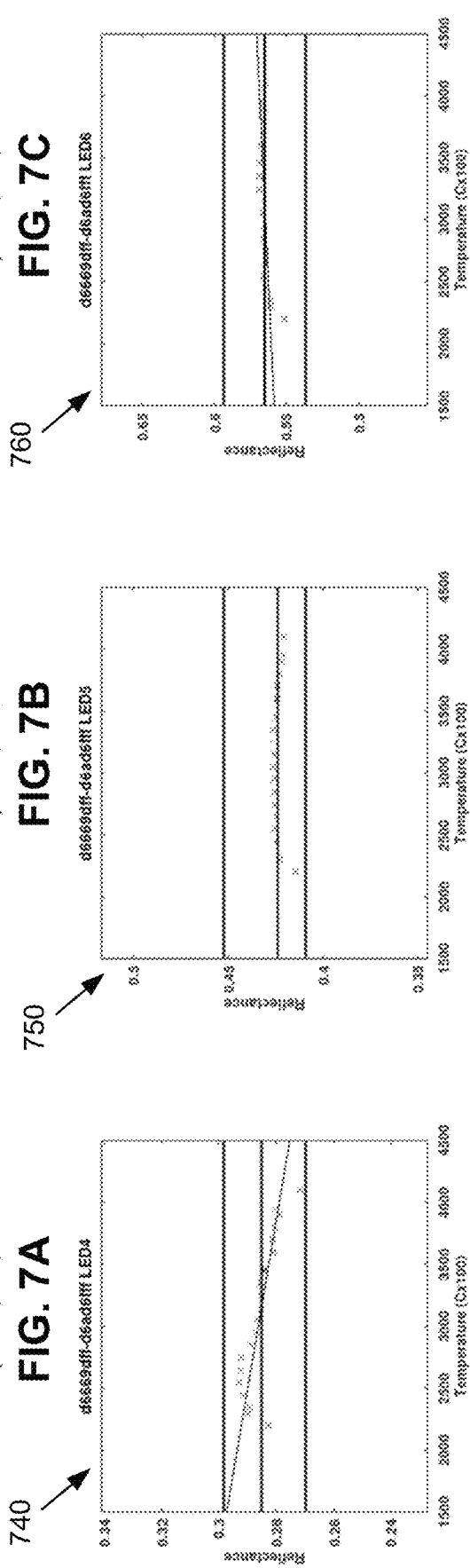

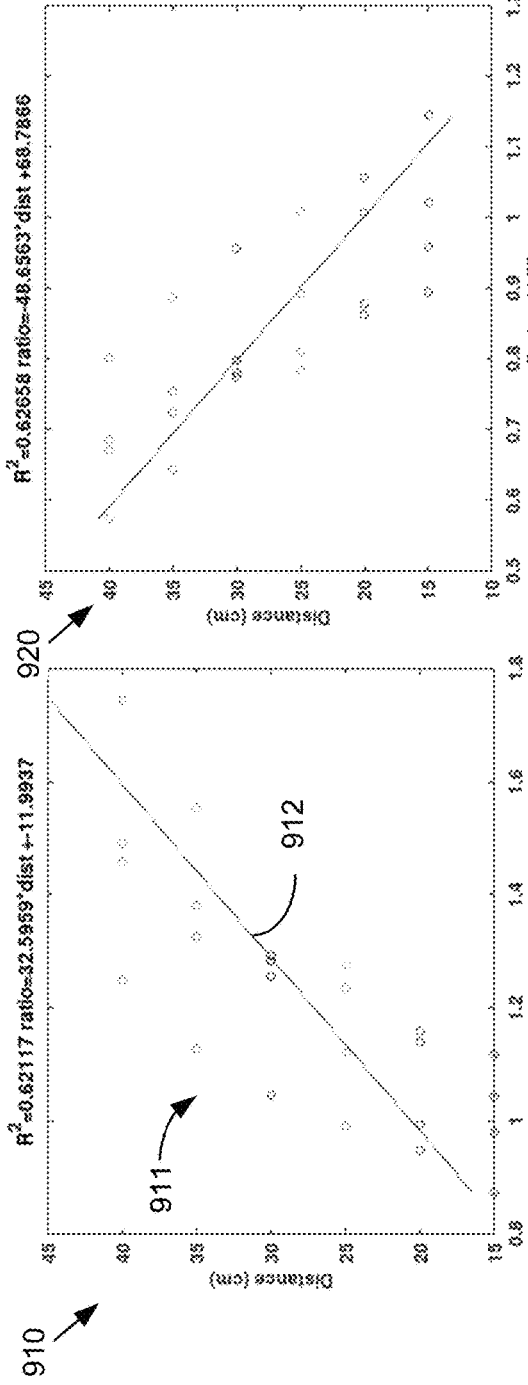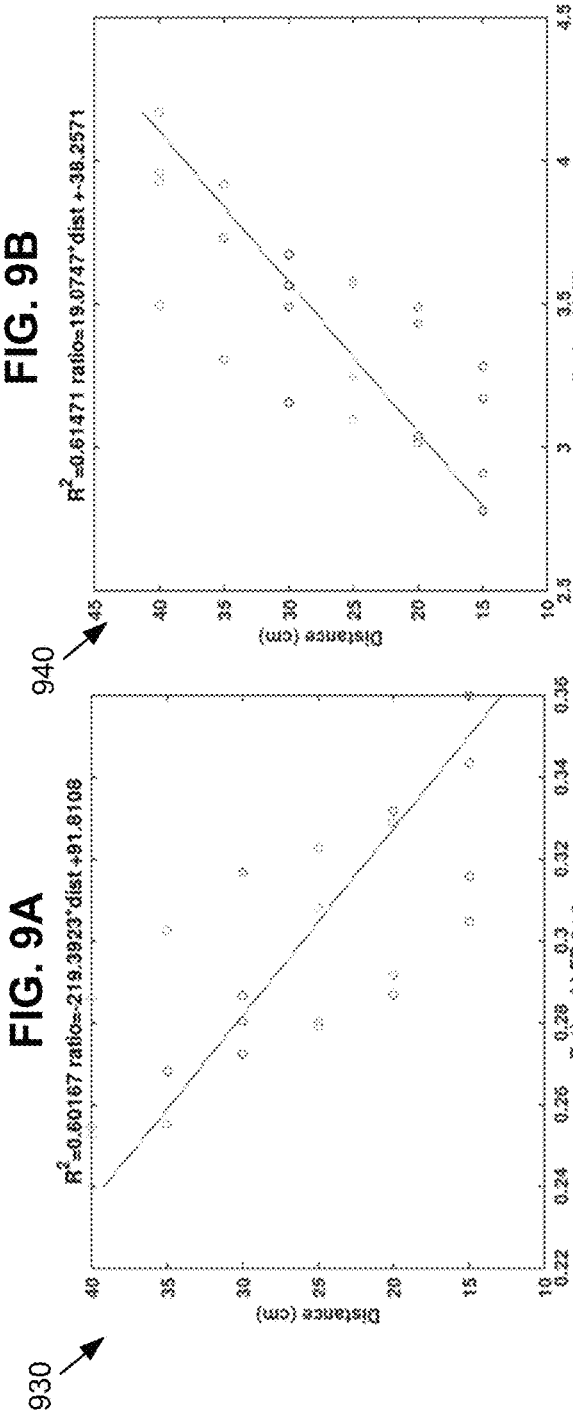
FIG. 9A
FIG. 9B
FIG. 9C
FIG. 9D

RELEASABLE PORTABLE IMAGING DEVICE FOR MULTISPECTRAL MOBILE TISSUE ASSESSMENT VIA DETERMINING DRIVING INTENSITY CORRECTION FOR LEDS

CROSS-REFERENCE TO RELATED PATENT APPLICATION

This application claims the benefit of U.S. Provisional Patent Application No. 63/315,493 filed Mar. 1, 2022; the entire contents of Patent Application 63/315,493 is hereby incorporated by reference.

FIELD

The various embodiments described herein generally relate to one or more devices, systems and methods for the visual assessment of a tissue region.

BACKGROUND

Wound progression, especially among individuals suffering from diabetes, is an important source of concern, both for individuals suffering from wounds and for the health care system. Indeed, individuals suffering from diabetes are much more likely than the general population to suffer from diabetic wounds and ulcers. If left untreated, these types of wounds can lead to a high risk of lower limb amputation and in some cases, can lead to death.

Early identification and regular monitoring of these wounds can reduce their socioeconomic burden and allow healthcare resources to be used more efficiently. Currently, diagnosis and management of wounds requires diabetic patients to regularly visit their primary care physician. Primary care physicians can detect early signs of tissue damage and monitor progression of wounds by observing the patient's skin. However, these visits are resource inefficient and time consuming, as in many cases, no life-threatening or limb-threatening damage is observed.

SUMMARY OF VARIOUS EMBODIMENTS

According to one broad aspect of the teachings herein, in at least one embodiment described herein there is provided a method for positioning a portable multispectral imaging device within a target distance range relative to a surface for imaging a region of interest (ROI) of the surface, wherein the method comprises: determining a distance between the portable multispectral imaging device and the ROI of the surface; determining whether the distance is within the target distance range; generating a signal indicating to a user that the portable multispectral imaging device is not within the target distance range and providing instructions to the user to guide that the user for repositioning the portable multispectral imaging device; and triggering an image capturing sequence when the portable multispectral imaging device is within the target distance range.

In at least one embodiment, determining the distance between the portable multispectral imaging device determining the distance between the portable multispectral imaging device and the ROI of the surface comprises obtaining N image datasets of the ROI by sensing reflectances using a light sensor when the ROI is illuminated by light generated sequentially by one of N LEDs of the portable multispectral imaging device where each LEDs emits light at a unique discrete wavelength and determining a distance between the LEDs of the portable multispectral imaging device and the surface based on the N image datasets.

In at least one embodiment, determining the distance between the portable multispectral imaging device and the surface comprises calculating at least one ratio between reflectances from two of the N image datasets and comparing the at least one calculated ratio with known distances associated with the at least one ratio.

In at least one embodiment, the method further comprises obtaining a reference image dataset by sensing reflectances when the ROI is not illuminated, determining inherent noise due to ambient environment during image acquisition from the reference image dataset and processing the N image datasets to remove the inherent noise.

In at least one embodiment, the method further comprises applying a temporal filter to the calculated distances.

In at least one embodiment, the method further comprises generating and displaying a positioning indicator overlaid onto an image of the ROI of the surface that is shown on a display to aid the user in positioning the portable multispectral imaging device so that the positioning indicator is moved towards a centre of the ROI of the surface.

In at least one embodiment, determining the distance between the portable multispectral imaging device and the ROI of the surface comprises obtaining, from a distance sensor, at least one measurement of the distance between the portable multispectral imaging device and the surface.

In at least one embodiment, the distance sensor is a light detection and ranging (LIDAR) sensor.

In at least one embodiment, the method further comprises applying to the at least one measurement a temporal filter to obtain a filtered distance measurement and wherein determining whether the distance is within the target distance range comprises determining whether the filtered distance measurement is within the target distance range.

In at least one embodiment, generating the signal indicating that the portable multispectral imaging device is not within the target distance range from the tissue region comprises generating one of: a signal indicating that the device is too close to the tissue region or a signal indicating that the device is too far from the tissue region.

In at least one embodiment, the method further comprises generating and displaying a distance indicator that is shown on a display to aid the user in positioning the portable multispectral imaging device.

In at least one embodiment, triggering the image capturing sequence comprises obtaining N image datasets of the ROI when the ROI is illuminated by a light signal having a unique discrete wavelength selected from N discrete unique frequencies.

In another aspect, in accordance with the teachings described herein, there is provided at least one embodiment of a method for calibrating a light source unit of a portable multispectral imaging device, wherein the method is performed by at least one processor and the method comprises: determining a desired reflectance intensity to image a region of interest (ROI) on a surface; determining a value of at least one parameter of at least one environmental condition affecting an actual reflectance measured when a light signal is emitted by the light source unit; determining a driving intensity correction factor based on the measured at least one parameter value to compensate for any changes in the at least one environmental condition to generate a standardized light intensity output so that a resulting light reflectance from the ROI that is detected by a light sensor of the portable multispectral imaging device is within a range of the desired reflectance intensity; and controlling an output intensity of the light source unit based on the driving intensity correction factor.

In at least one embodiment, determining the value of the at least one parameter comprises obtaining an estimate of a temperature of the light source unit when the voltage and current provided to the light source unit is held constant.

In at least one embodiment, determining the value of the at least one parameter affecting an actual reflectance of the light signal emitted by the light source further comprises: obtaining an estimate of a voltage of the light source unit; and obtaining an estimate of a current of an emitter circuit of the light source unit.

In at least one embodiment, determining the value of the at least one parameter affecting an actual reflectance of the light signal emitted by the light source further comprises obtaining an estimate of a voltage of the light source unit and obtaining an estimate of a current of an emitter circuit of the light source unit.

In at least one embodiment, the light source unit includes a plurality of LEDs and the method comprises determining the driving intensity correction factor for each of the LEDs.

In at least one embodiment, each driving intensity correction factor is determined by using the measured at least one parameter value as input into a lookup table for each LED, using one or more correction curves or using a polynomial that is defined over an output intensity range for each LED.

In another aspect, in accordance with the teachings herein there is provided at least one embodiment of a portable multispectral imaging device for imaging a region of interest (ROI) on a surface, wherein the portable imaging device comprises: a light sensor for obtaining image datasets of the ROI when the ROI is illuminated; a light source unit comprising an array of LEDs radially disposed around the light sensor for illuminating the ROI of the tissue surface during image capture; and an emitter circuit operatively coupled with the light source unit and operable to generate control signals for controlling output light intensity of the array of LEDs, where a driving intensity correction factor is applied to at least one of the control signals of at least one of the LEDs to compensate for a change in at least one environmental condition to generate a standardized light intensity output so that a resulting light reflectance from the ROI that is detected by the light sensor is within a range of a desired reflectance intensity.

In at least one embodiment, the portable multispectral imaging device further comprises: a diffusive element that is located to cover the array of LEDs for diffusing light emitted by the array of LEDs, the diffusive element also including an aperture where the light sensor is positioned; and a light shield for shielding the light sensor from the light emitted by the array of LEDs.

In at least one embodiment, the LEDs are radially disposed on a board with an aperture that is aligned with a central axis of the light sensor, and the light shield includes an upper rib for resting on a portion of the board adjacent the aperture in the board and the shield includes a lower housing portion for housing the light sensor.

In at least one embodiment, the emitter circuit comprises a drive circuit that generates drive current signals based on the driving intensity correction factor for each LED; a multiplexer unit coupled to the drive circuit for receiving the drive current signals; LED drivers coupled to the drive circuit for receiving the drive current signals and generating the control signals to control a light output intensity for each of the LEDs; and a controller circuit that is operably coupled to the drive circuit and includes a processor that is operable to determine the driving intensity correction factor for each LED for collectively emitting the standardized light intensity output.

In at least one embodiment, the drive circuit comprises: a battery unit having at least one battery; a charge level monitor coupled to the battery unit, the charge level monitor being operable to monitor a battery voltage of the battery unit; a voltage regulator stage that has at least one voltage regulator and is configured for maintaining the voltage of the battery unit within a desired voltage range; a charge management controller that is configured for managing a charge level of the battery unit based on the monitored battery voltage of the battery unit; and a current regulator stage for generating the drive current signals.

In at least one embodiment, the charge management controller is coupled to an external power source for charging the battery unit so that the monitored voltage is within the desired voltage range.

In at least one embodiment, the at least one environmental condition includes temperature, and the controller circuit is operable to control the intensity of the array of LEDs based on a temperature of the array of LEDs.

In at least one embodiment, the at least one environmental condition includes temperature, voltage and current, and the controller circuit is operable to control the light output intensity of the array of LEDs based on a temperature of the LEDs when the voltage and current provided to the light source unit is held constant, a monitored voltage of the battery unit; and a measured current of the drive circuit.

In at least one embodiment, a thermistor is included for measuring the temperature of the array of LEDs, preferably the temperature being a junction temperature.

In at least one embodiment, the light sensor is a near infrared sensor.

In at least one embodiment, the portable multispectral imaging device further comprises a communication unit for communicating with an electronic device.

In at least one embodiment, a processor is included that is configured to perform the any one of the methods described in accordance with the teachings herein.

In another aspect, in accordance with the teachings herein there is provided at least one embodiment of a system for performing remote tissue assessment of a tissue region, wherein the system comprises: a portable multispectral imaging device that is defined according to any one of the embodiments described herein; and an electronic device in communication with the portable imaging device, the electronic device comprising a device processor for processing the N image datasets.

In at least one embodiment, the portable multispectral imaging device is in communication with the electronic device via a USB connection.

In at least one embodiment, the electronic device is a mobile device.

It will be appreciated that the foregoing summary sets out representative aspects of embodiments to assist skilled readers in understanding the following detailed description. Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIGS. 4A-4F show graphical examples of reflectance over a range of intensities using an example embodiment of the portable imaging device of FIG. 1.

FIGS. 7A-7F show graphical examples of illumination output intensity when the portable imaging device is calibrated.

FIGS. 9A-9D show graphical examples of how distance varies as a function of a ratio of reflectances for certain LEDs of the portable imaging device.

Figure 1:
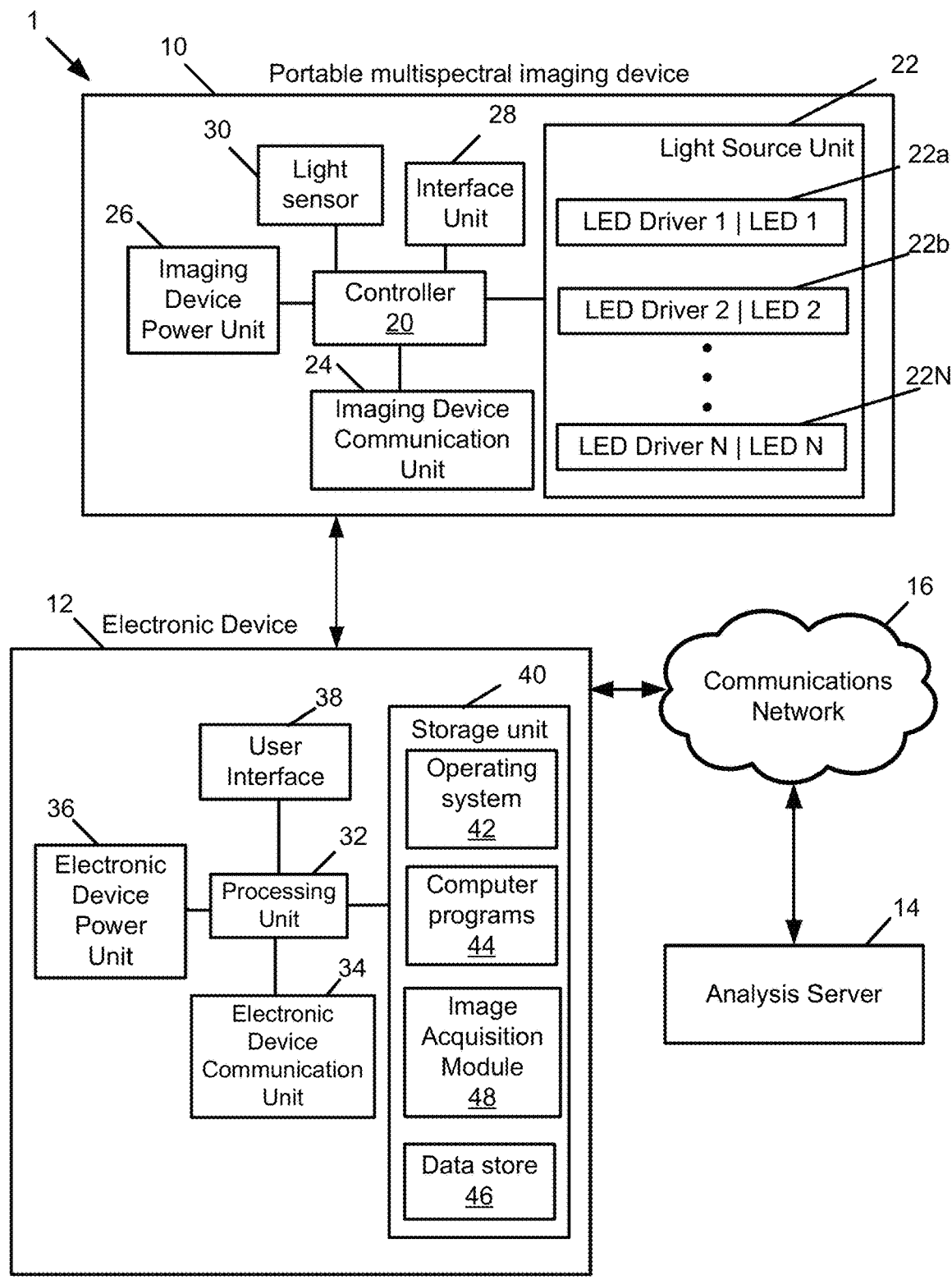
FIG. 1 is a block diagram of an example embodiment of a system including a portable imaging device and a mobile device that may be used for visual tissue assessment where the images and/or results may be communicated to remote devices.

Further aspects and features of the example embodiments described herein will appear from the following description taken together with the accompanying drawings.

DETAILED DESCRIPTION OF THE EMBODIMENTS

The headings and Abstract of the Disclosure provided herein are for convenience only and do not interpret the scope or meaning of the embodiments.

Various embodiments in accordance with the teachings herein will be described below to provide examples of at least one embodiment of the claimed subject matter. No embodiment described herein limits any claimed subject matter. The claimed subject matter is not limited to devices, systems or methods having all of the features of any one of the devices, systems or methods described below or to features common to multiple or all of the devices, systems or methods described herein. It is possible that there may be a device, system or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements or steps. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending on the context in which these terms are used. For example, the terms coupled or coupling can have a mechanical, electrical or communicative connotation. For example, as used herein, the terms coupled or coupling can indicate that two elements or devices can be directly connected to one another or connected to one another through one or more intermediate elements or devices via an electrical element, an electrical signal or a mechanical element depending on the particular context.

Unless the context requires otherwise, throughout the specification and claims which follow, the word "comprise" and variations thereof, such as, "comprises" and "comprising" are to be construed in an open, inclusive sense, that is, as "including, but not limited to".

Various terms used throughout the present description may be read and understood as follows, unless the context indicates otherwise: singular articles and pronouns as used throughout include their plural forms, and vice versa; similarly, gendered pronouns include their counterpart pronouns so that pronouns should not be understood as limiting anything described herein to use, implementation, performance, etc. by a single gender. Further definitions for terms may be set out herein; these may apply to prior and subsequent instances of those terms, as will be understood from a reading of the present description.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies.

Furthermore, the recitation of numerical ranges by endpoints herein includes all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

Reference throughout this specification to "one embodiment", "an embodiment", "at least one embodiment" or "some embodiments" means that one or more particular features, structures, or characteristics may be combined in any suitable manner in one or more embodiments, unless otherwise specified to be not combinable or to be alternative options.

As used in this specification and the appended claims, the singular forms "a," "an," and "the" include plural referents unless the content clearly dictates otherwise. It should also be noted that the term "or" is generally employed in its broadest sense, that is, as meaning "and/or" unless the content clearly dictates otherwise.

Similarly, throughout this specification and the appended claims the term "communicative" as in "communicative pathway," "communicative coupling," and in variants such as "communicatively coupled," is generally used to refer to any engineered arrangement for transferring and/or exchanging information. Examples of communicative pathways include, but are not limited to, electrically conductive pathways (e.g., electrically conductive wires, physiological signal conduction), electromagnetically radiative pathways (e.g., radio waves), or any combination thereof. Examples of communicative couplings include, but are not limited to, electrical couplings, magnetic couplings, radio couplings, or any combination thereof.

Throughout this specification and the appended claims, infinitive verb forms are often used. Examples include, without limitation: "to detect," "to provide," "to transmit," "to communicate," "to process," "to route," and the like. Unless the specific context requires otherwise, such infinitive verb forms are used in an open, inclusive sense, that is as "to, at least, detect" "to, at least, provide," "to, at least, transmit," and so on.

A portion of the example embodiments of the systems, devices, or methods described in accordance with the teachings herein may be implemented as a combination of hardware or software. For example, a portion of the embodiments described herein may be implemented, at least in part, by using one or more computer programs, executing on one or more programmable devices comprising at least one processing element, and at least one data storage element (including volatile and non-volatile memory). These devices may also have at least one input device (e.g., a keyboard, a mouse, a touchscreen, and the like) and at least one output device (e.g., a display screen, a printer, a wireless radio, and the like) depending on the nature of the device.

It should also be noted that there may be some elements that are used to implement at least part of the embodiments described herein that may be implemented via software that is written in a high-level procedural language such as object-oriented programming. The program code may be written in C, C++ or any other suitable programming language and may comprise modules or classes, as is known to those skilled in object-oriented programming. Alternatively, or in addition thereto, some of these elements implemented via software may be written in assembly language, machine language, or firmware as needed.

At least some of the software programs used to implement at least one of the embodiments described herein may be stored on a storage media or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions, such as program code, for one or more processors. The program code may be preinstalled and embedded during manufacture and/or may be later installed as an update for an already deployed computing system. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g., downloads), media, digital and analog signals, and the like. The computer useable instructions may also be in various formats, including compiled and non-compiled code.

Accordingly, any module, unit, component, server, computer, terminal or device described herein that executes software instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information, and which can be accessed by an application, module, or both. Any such computer storage media may be part of the device or accessible or connectable thereto.

Described herein are various methods and devices which may be used along with the processing methods of the multispectral imaging device described in PCT Application Publication No. WO 2018/035612 filed on Aug. 24, 2017, the entirety of which is incorporated herein by reference, for performing multispectral mobile tissue assessment.

The various example embodiments of the portable multispectral imaging device described herein are capable of receiving reflected and back-scattered photons that may be used to capture multispectral images of a tissue region. Using reflectance data captured in these multispectral images, tissue assessment for a physiological condition can be performed to provide an early warning for the occurrence of the physiological condition or for a worsening status of the physiological condition.

Spectral imaging entails using a light source for illuminating a region of interest (ROI) with a distinct wavelength of the electromagnetic spectrum, capturing an image of the illuminated ROI using a light sensor having appropriate spectral sensitivity, and then sequentially repeating this process across several wavelengths to obtain a spectral dataset. The resulting spectral dataset contains images of the same ROI across several illuminations of differing wavelengths. The light source comprises a plurality of LEDs, hereafter referred to as an LED system, that have different peak wavelengths corresponding with the aforementioned-distinct wavelengths. The light source and the light sensor are provided in a portable multispectral imaging device defined according to one of the embodiments described in accordance with the teachings herein.

The strongest absorbers within the illuminated biological tissue at the LED peak wavelengths are species of hemoglobin, including a combination of oxygenated hemoglobin, deoxygenated hemoglobin and dyshemoglobins. The portable multispectral imaging device can therefore be used for non-contact illumination of biological tissue to yield functionally significant physiological parameters of superficial tissue, such as oxygen saturation and relative abundances of hemoglobin species. The LED peak wavelengths can be in the visible light range such as, but not limited to, in the range of about 200 nm to about 1000 nm, preferably in the range of 620 nm to 980 nm, for example. In an alternative embodiment, the LED system can span a further range of spectral bandwidths to include shorter and longer wavelengths such as, but not limited to, light waves in the range of about 600 nm to 1000 nm, ultraviolet light in the range of about 200 nm to about 400 nm and short-wave infrared light in the range of about 1400 nm to about 3000 nm, for example.

The portable multispectral imaging device is hand-held and can be easily manipulated with one hand in order to obtain images for any ROI such as tissue regions for many different body parts. The device is also easy to use. Accordingly, in at least some embodiments, the portable multispectral imaging device can be used by lay people to assess tissue health at various remote locations with respect to a medical institution (e.g., a hospital, clinic or the like), such as a person's home. Accordingly, the portable multispectral imaging device may be used for rapid assessment of wounded tissue, non-wounded tissue and tissue health in a variety of locations relative to a medical institution. For example, the portable multispectral imaging device may be used to investigate and monitor non-wounded tissue for pressure injury formation and for imaging tissue regions prior to and following vascular interventions. However, the portable multispectral imaging device may also be used by medical personnel at the medical institution.

In at least one example embodiment, the portable multispectral imaging device may be incorporated with wound management software that implements a wound tracking system that can be used to automate follow up appointments and provide early warning for the detection of negative tissue changes thereby alerting physicians, clinicians or healthcare workers to patients requiring further assessment and intervention such as receiving a new dressing, surgery and the like. This will reduce the number of hospital visits and permit early detection of tissue ischemia.

In at least one example embodiment described in accordance with the teachings herein, the portable multispectral imaging device may be used to obtain image data for a sequence of images of a tissue region for a portion of a body part. The sequence of images may be obtained while illuminating a tissue region with a sequence of different wavelengths of visible and Near InfraRed (NIR) light so that each image is obtained while illuminating the tissue region with light having a different wavelength. A reference image can be obtained when the tissue region is not illuminated by light for use in accounting for and removing the inherent noise in the other images of the tissue region that were obtained during illumination. Each of the images can include reflectance data. It should be understood that each of the obtained images are stored as digital data.

The body part that is imaged can be any part of a person or an animal. For example, the body part can be, but is not limited to, a leg, a foot, a finger, or a hand. By comparing the image data for the different images obtained at different wavelengths, it may be determined how much oxygen saturation and relative abundance of hemoglobin species exist in the imaged tissue. The imaged tissue can include skin, muscle, ligaments, vasculature and/or bones.

The imaging can be performed for a variety of conditions in which it is important to perform tissue monitoring such as, but not limited to, monitoring diabetic ulcers, for example. By early recognition and screening of diabetics, it may be possible to save limbs and lives. For example, diabetic patients can have both small and large vessel peripheral vascular diseases. These features can lead to chronic ischemia of the lower extremities and predispose these patients to limb ulceration. The lower extremities can be imaged using the portable multispectral imaging device to determine if a variety of physiological conditions exist and if so, the severity of the physiological condition, thereby allowing for tissue viability to be assessed. In contrast, conventional monitoring techniques may be limited to monitoring for particular conditions such as the existence of ischemia or the physical measurement of a wound (and if so, the severity of the ischemia).

Referring now to FIG. 1, shown therein is a block diagram of an example embodiment of a system 1 that can be used for remote multispectral tissue assessment. The system 1 includes a portable multispectral imaging device 10 that includes a light source unit 22 and a camera 30, and an electronic device 12 that includes a processing unit 32. The electronic device 12 may be a mobile device such as a smart phone, a laptop, a tablet or another suitable mobile electronic device. In an alternative embodiment, the electronic device 12 may not be mobile and may instead be a desktop computer, for example.

The different discrete visible light and NIR wavelengths that are used during imaging may be specifically chosen to measure a particular physiological marker of interest. The methodology that is employed only requires a small number of wavelengths which reduces the hardware requirements of the light source unit 22 of the portable multispectral imaging device 10. The light source unit 22 includes light sources that are used to generate N different light signals are generated where N is the number of physiological markers being measured in the obtained images. The parameter N is an integer that is small to reduce the hardware requirements of the light source unit 22, such as, but not limited to, N<6, for example. It will, however, be understood that the parameter N can be any integer number with an upper limit defined by the size of the light source unit 22 and the physical footprint of the portable multispectral imaging device 10. Accordingly, the light source unit 22 can include only N monochromatic light sources such as N monochromatic LEDs. Alternatively, the light sources can be provided in pairs emitting a light signal with the same wavelength, in which case the light source unit 22 can include 2N monochromatic light sources such as 2N monochromatic LEDs.

The portable multispectral imaging device 10 includes a controller 20, the light source unit 22 having a plurality of LED drivers with LEDs 22a to 22N, an imaging device communication unit 24, an imaging device power unit 26, an interface unit 28 and a camera or sensor 30. The controller 20 typically includes at least one processor and memory. The memory is used to store software that, when executed by the processor of the controller, configures the controller 20 for generating light control signals such that the light source unit 22 generates light signals having selected parameters such as a desired frequency output light illumination (i.e., light intensity). The portable multispectral imaging device 10 may include additional or alternative elements in other embodiments. For example, the portable multispectral imaging device 10 may additionally include a distance sensor (not shown). As another example, instead of using LEDs that generate light having a single wavelength, LEDs which are controllable to generate light at several different discrete wavelengths may be used.

In this example embodiment, the LEDs 22a to 22N are monochromatic, visible light or NIR, light emitting diodes that are controlled by the controller 20 which generates a light control signal that is sent to the light source unit 22. The controller 20 can use the light control signal to control the LED drivers 1 to N to regulate both light intensity as well as light emission duration (e.g., +/−8 microseconds) for the light signals that are generated by the LEDs 1 to N. Alternatively, the controller 20 may generate a separate light control signal for each of the LED drivers 1 to N to individually regulate the light intensity and the light emission duration of each of the light signals generated by the LEDS 22a to 22N. The LEDs 22a to 22N may be selected to have a particular wavelength in the range of about 600 nm to about 1,000 nm. The particular wavelength range may be determined based on the wavelengths that are considered as being optimal according to the physiological markers that are to be measured from the image datasets that are obtained by the portable multispectral imaging device 10.

The LEDs 22a to 22N are generally high powered (e.g., about 3-5 Watts). In at least one embodiment, larger amounts of power can be used for the LEDs 22a to 22N that generate light at longer wavelengths to counteract the lower sensitivity of the light sensor 30 of the imaging device 10 at longer wavelengths. However, the intensity of the generated light signals depends on the sensitivity of the light sensor 30 to the visible light or NIR wavelengths used in these light signals as well as for providing output light illumination that allows for images to be obtained under standardized conditions in accordance with the teachings herein.

In an alternative embodiment, a larger number of visible light or NIR wavelengths and therefore a larger number of LEDs can be used to obtain more image data sets that can be used to reduce error in determining the values for the physiological marker maps from the obtained image datasets. However, using monochromatic LEDs, the footprint of the light source unit 22 increases by the number of wavelengths that are used in obtaining the image datasets.

The light sensor 30 senses reflected light from the surface of the ROI being imaged and the sensed light is then digitized and converted to image datasets of the ROI. The light sensor 30 can be any optical, optoelectrical camera or sensor that is sensitive to visible or NIR light in the range of about 600 nm to 1000 nm. For example, the light sensor 30 can be a camera sensitive to reflected radiation in the range of about 200 nm to about 1000 nm, preferably in the range of about 620 nm to about 980 nm, for example. In an alternative embodiment, the light sensor 30 system can be sensitive to a further range of spectral bandwidths to include shorter and longer wavelengths such as, but not limited to, light waves in the range of about 600 nm to 1000 nm, ultraviolet light in the range of about 200 nm to about 400 nm and short-wave infrared light in the range of about 1400 nm to about 3000 nm, for example. In at least one embodiment, the light sensor 30 may be a standard cell phone camera without the infrared filter.

The imaging device communication unit 24 allows the portable multispectral imaging device 10 to communicate with the electronic device 12. The imaging device communication unit 24 can include a USB interface so that the portable multispectral imaging device 10 may be releasably couplable to the electronic device 12. Alternatively, the communication unit 24 can be a Bluetooth radio or a WiFi radio and the controller 20 can communicate with the electronic device 12 over a Bluetooth Serial Port Protocol connection or a WiFi connection, respectively. In either of these cases, the portable multispectral imaging device 10 may be releasably couplable to the electronic device 12. This advantageously allows the same portable multispectral imaging device 10 to be used with a variety of different electronic devices.

Figure 3:
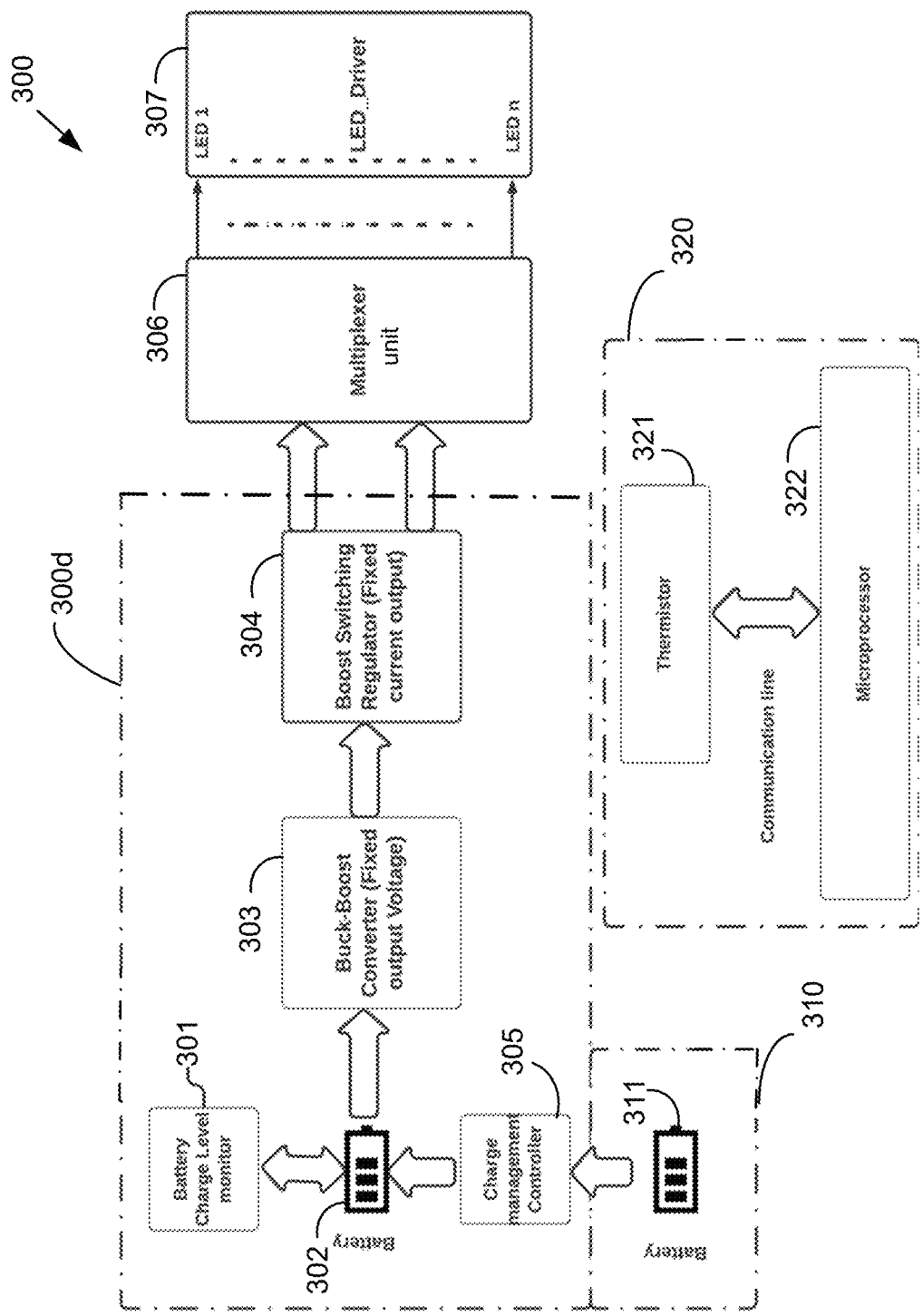
FIG. 3 is a block diagram of an example embodiment of circuitry used for calibrating and generating light signals for the portable imaging device of FIG. 1 with standardized illumination output intensity.

The imaging device power unit 26 provides power to the electronic components of the portable multispectral imaging device 10. Accordingly, the imaging device power unit 26 generally includes a voltage regulator that can be coupled to one or more lithium polymer batteries that are used to provide enough current to flow to the LEDs 22a to 22N. For example, the battery can be selected to provide about 2 A peak power to drive the LEDs 22a to 22N. The interface unit 28 includes off board connectors such as a battery connector to connect the imaging device power unit 26 to the battery. In an alternative embodiment, the battery may be rechargeable in which case the imaging device power unit 26 may be coupled to the electronic device 12. Another example embodiment of the circuitry that may be used with the imaging device power unit 26 is shown in FIG. 3.

The imaging device power unit 26 can be coupled to the electronic device 12 via an appropriate interface such as a USB interface to receive power from the electronic device 12. For example, the interface unit 28 can include a USB (i.e., Firewire interface) port to allow the portable multispectral imaging device 10 to electrically connect to the electronic device 12 to receive power therefrom which is then regulated by the portable multispectral power unit 26. For example, the electronic device 12 may provide power to recharge the battery of the portable multispectral imaging device 10. The imaging device communication unit 24 allows the portable multispectral imaging device 10 to communicate with an electronic device communication unit 34 of the electronic device 12 in order to transmit digital images acquired by the light sensor 30 to the electronic device 12 and for receiving instructions from the electronic device 12. In at least one embodiment, the electronic device 12 may process the acquired digital images for providing the tissue assessment. Alternatively, in at least one embodiment, a processor of the portable multispectral imaging device may be configured to process the acquired digital images for providing the tissue assessment. In either case, the processing that is done to the acquired images may be done as described in published PCT patent application WO2018/035612A1.

The electronic device 12 includes a processing unit 32, the electronic device communication unit 34, an electronic device power unit 36, a user interface 38, and a storage unit 40. The user interface 38 may include various input devices, output devices and/or input/output devices. For example, the user interface 38 may include a display for showing various images and data to the user of the system 10 and a keyboard and/or mouse to allow the user to provide control data to the electronic device 12. The storage unit 40 can be implemented using various types of memory hardware and used to store various software code such as code for an operating system 42, computer programs 44, and a data store 46. The electronic device 12 also includes an image acquisition module 48 that can be used to receive image datasets captured by the imaging device 10. The embodiment of the electronic device 12 shown in FIG. 1 is an example and there can be additional or alternative elements that are included in other embodiments of the electronic device 12.

The processing unit 32 controls the operation of the electronic device 12 and includes one or more suitable processors that can provide sufficient processing power depending on the configuration and requirements of the electronic device 12 as is known by those skilled in the art. For example, the processing unit 32 may include one or more high performance processors. In alternative embodiments, specialized hardware can be used to provide some of the functions provided by the processing unit 32. The processing unit 32 communicates with at least one other component, such as the electronic device communication unit 34 and/or the user interface 38, in order to receive or send data. For instance, in at least one example embodiment, the processing unit 32 may receive image data sets that are obtained by the portable multispectral imaging device 10. The processing unit 32 can also process and analyze the image datasets obtained by the portable multispectral imaging device 10 in at least one embodiment. Alternatively, in at least one embodiment, some or all of the processing and analysis may be performed by the processor(s) of the portable multispectral imaging device 10.

The electronic device 12 may be configured to run or execute software instructions of the image acquisition module 48 which may be implemented as a software application that coordinates the communication between the electronic device 12 and the imaging device 10. The image acquisition module 48 may be operable to acquire image datasets using the light source unit 22 and the camera 30 of the portable multispectral imaging device 10. These acquired image datasets may then be processed as described herein.

In some embodiments, once acquired, the image datasets can be stored on the data store 46 and can then be sent to the analysis server 14 by the electronic device communication unit 34 for analysis. The electronic device communication unit 34 uses a communication protocol that corresponds to the communications protocol being used by the communications network 16 that links the electronic device 12 with other computing devices such as the analysis server 14. Advantageously, the computing power of the analysis server 14 can be used to process and analyze the image datasets obtained by the portable multispectral imaging device 10 in at least one embodiment.

In such embodiments, the electronic device 12 and the analysis server 14 communicate via the communications network 16. The communications network 16 can be any suitable communication network depending on the particular implementation of the overall system. For example, the portable multispectral imaging device 10 may be used in a medical institution in which case the communications network 16 may be an internal institutional network, such as a hospital network, that may be implemented using suitable type of network architecture and communication protocol such as an Intranet. In other cases, the communications network 16 can be an external network such as the Internet or another external data communications network, which is accessible by using a web browser on the electronic device 12 to browse one or more web pages presented over the Internet by a web portal module.

In at least one embodiment, the portable multispectral imaging device 10 may be able to communicate with other devices over the network via the imaging device communication unit 24. This may be done when acquired images by the portable multispectral imaging device 10 are directly sent to other devices instead of or in addition to sending the acquired images to the electronic device 12. In at least one embodiment, the controller 20 may be configured to perform the processing and analysis of the acquired images to perform the tissue assessment and then send the results of the tissue assessment to the electronic device 12 or to a remote device via the communications network 16.

Figure 2:
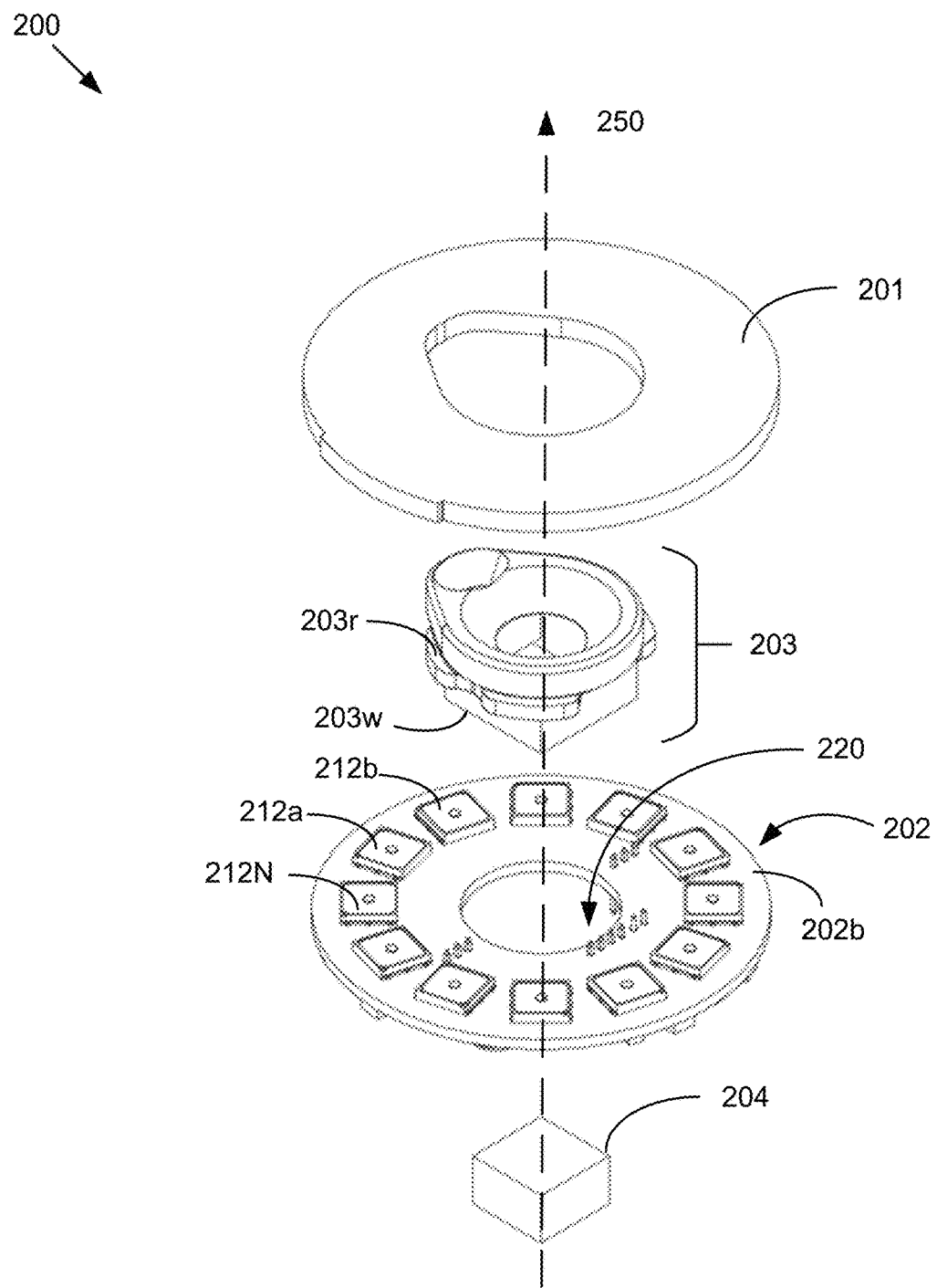
FIG. 2 is an exploded view of some components of an example embodiment of the portable imaging device of FIG. 1.
Figure 11:
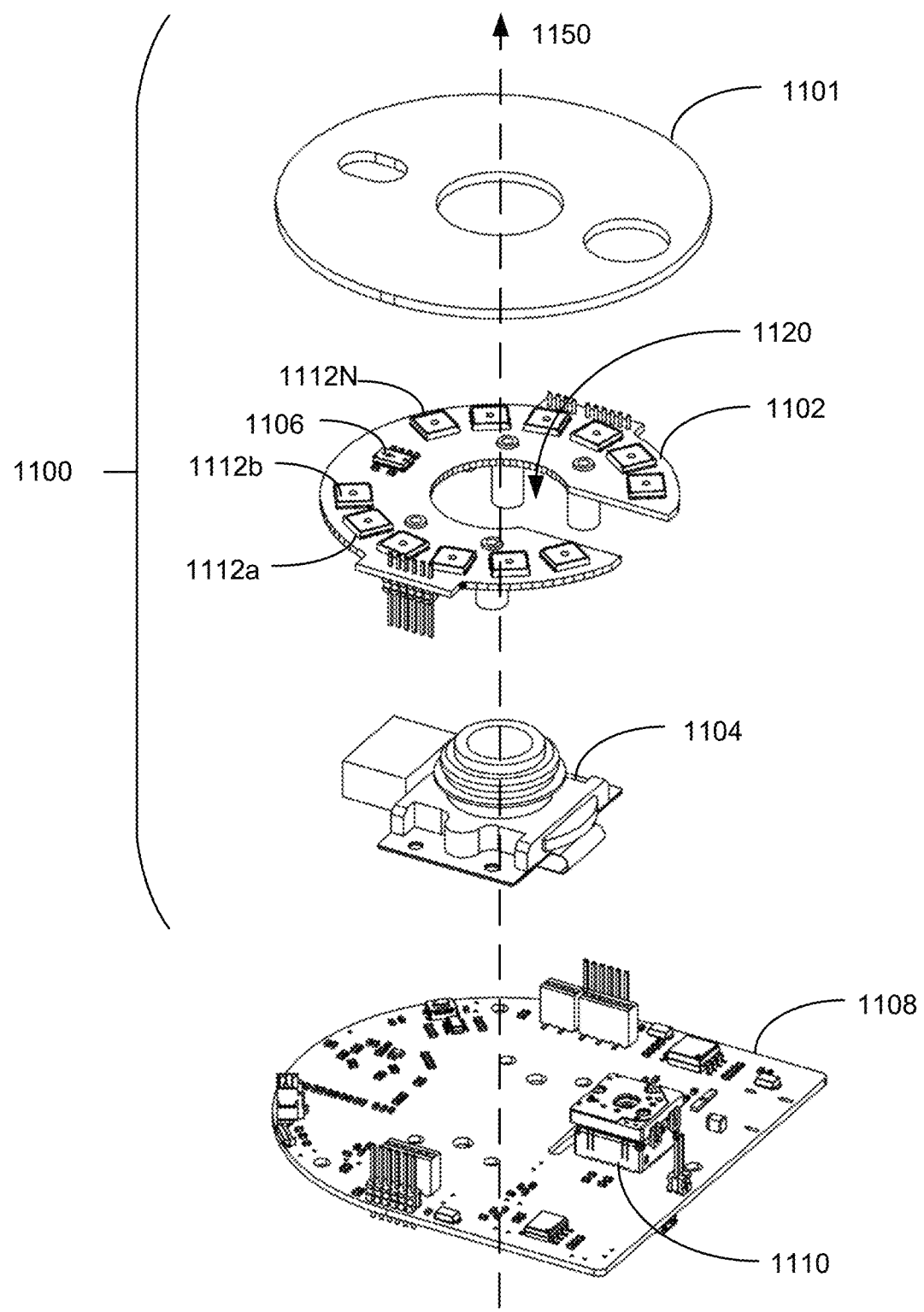
FIG. 11 is an exploded view of some components of another example embodiment of the portable imaging device.

Referring now to FIG. 2, shown therein is an exploded view of an example embodiment of the optical hardware 200 that may be used by the portable multispectral imaging device 10. The optical hardware 200 includes a light sensor (e.g., a camera) 204 and a light source unit 202, a light shield 203 and a diffusing element 201 (e.g., a diffuser). The light sensor 204, the light source unit 202, the shield 203 and the diffusing element 201 can be disposed in a concentric fashion relative to one another about a common central axis 250. In at least one embodiment, the diffuser 201 may be optional if a lens that can perform similar functions is incorporated in its place. The optical hardware 200 can be connected to a circuit board, on which a processing unit can be mounted (an example embodiment of this is shown in FIG. 11).

In at least one embodiment, the light shield 203 has a high absorption of light in a wavelength range where the LEDs are emitting light such as, but not limited to between about 600 to about 1000 nm for example, so that a negligible amount of emitted light is detected at the light sensor 204 from the light source unit 202 directly. Alternatively, in at least one embodiment, the light shield 203 may be optional where there are direct or indirect paths for light to scatter back into the light sensor 204.

The light source unit 202 is operable to illuminate a particular region of interest under control by the controller 20, for example, and the light sensor 204 captures image datasets of the light that is reflected back from the region of interest during illumination. In at least one embodiment, the light source unit 202 is adapted to provide enough illumination such as, but not limited to, about 2-3 Watts of LED power so that reflectance signals from the ROI can be detected by the light sensor 204. The light sensor 204 can capture images when the ROI is illuminated by the light source unit 202 and also when the ROI is not illuminated by the light source unit 202.

The light source unit 202 generally includes a printed circuit board 202b with various electrical components including LEDs 212a-212N, only a few of which are numbered for ease of illustration. The LEDs 212a-212N that can be radially disposed around the light sensor 204 such that the angular distance between adjacent LEDs is similar. The light source unit 202 can also include an aperture 220 in the circuit board 202b that aligns with the light sensor 204 so that the light sensor 204 can acquire images without obstruction from the various components of the light source unit 202. The LEDs 212a-212N can be radially disposed around the aperture 220. The light source unit 202 can also include electronic components that may be used to power or control the operation of the light source unit 202, as will be described in further detail with reference to FIG. 3.

As described with reference to FIG. 1, the light sensor 204 may be any type of optical, optoelectrical camera or sensor that is sensitive to light reflected by the region of interest when illuminated by the light source unit 202. In the example embodiment shown in FIG. 2, the light sensor 204 is an infrared sensor. The light sensor 204 can be activated for a short period in the range of about 16 ms to 70 ms to obtain an image, to minimize any noise in the obtained image that is due to patient or device motion. The light sensor 204 can be operable to obtain an image when instructed by the user and/or during successive image capture via software instructions. In at least one embodiment, the light sensor 204 may acquire image data at a frame rate of about 30 frames per second (e.g., every 33 ms).

In at least one embodiment, the diffusive element 201 may be placed on one or more of the LEDs 212a-212N. For example, the diffusive element 201 may cover the surface of the light source unit 202 and diffuse the light signal generated by the light source unit 202 to provide a more even light distribution when the ROI is being illuminated. The diffusive element 201 may be an off the shelf component that may be made sufficiently translucent to evenly scatter the light signals generated by the light source unit 202. For example, a mechanical tumbler may be used to physically process the surface of the diffusive element 201 to increase the scatter. The amount of scatter that is provided by the diffusive element 201 is relative to the optical properties of the light source unit 202, and the light sensor 204.

The shield 203 shields the light sensor 204 to prevent light signals emitted by the light source unit 202 from directly striking the light sensor 204 without first being reflected by the tissue region. Additionally, the shield 203 may prevent light signals emitted by the light source unit 202 from directly striking the light sensor 204 without first passing through the diffusive element 201. The shield 203 can be made of any material capable absorbing a high amount of light in the wavelength range of the light emitted by the light source unit 202 such as, but not limited to, about 600 nm to about 1000 nm, to prevent light emitted by the light source unit 202 from directly striking the light sensor 204. For example, the material used can be a stiff plastic, such as the Visijet® Armor M2G-CL, and can have a dark color, such as black, for example, to increase light absorption. The shield 203 may be disposed in the aperture 220 of the light source unit 202 such that an annular rib 203r sits on a portion of the board 202b that encircles the aperture 220. The shield 203 includes a lower housing portion 203w which is a hollow walled portion that slidingly receives the light sensor 204 to make a friction fit to hold the light sensor 203 in a stable position relative to the other optical components 200.

Referring now to FIG. 3, shown therein is a block diagram of an example embodiment of circuitry which may be used for calibrating and generating light signals for the portable multispectral imaging device with standardized illumination output intensity in accordance with the teachings herein. The block diagram shows an emitter circuit 300 which has a drive circuit 300d that is used to generate drive current signals that are provided as control signals to the LEDs 22a-22N to control the light output of each of them so that they collectively produce light with a standardized light intensity, a controller circuit 320 in electrical communication with the drive circuit 300d and an external power source 310 in electrical communication with the drive circuit 300d. While the circuitry is described with respect to the light source unit 22 of FIG. 1, it should be understood that it can be used with the optical components 200 and 1000 shown in FIGS. 2 and 10, respectively.

The emitter circuit 300 includes components used to monitor and regulate the voltage and current that is applied to the LEDs of the light source unit 22. The components of the emitter circuit 300 can be mounted on the printed circuit board of the light source unit 22.

For example, the drive circuit 300d can include a battery charge level monitor 301, a battery unit 302, a voltage regulator stage 303, a current regulator stage 304, and a charge management controller 305. The outputs of the drive circuit 300d are provided to a multiplexer unit 306 and LED Drivers 307 when then are sent as control signals for driving the output of each of the LEDs 22a-22N.

The battery unit 302 may include one or more batteries. If multiple batteries are used, then they are connected in parallel with one another. Each battery of the battery unit 302 may be a lithium polymer battery. The battery unit 302 is connected to the battery charge level monitor 301, which can be configured to monitor the voltage of the battery unit 302. For example, the battery charge level monitor 301 may be a fuel gauge sensor, such as, but not limited to a lithium-ion integrated circuit, capable of measuring the current drawn by the battery unit 302 and the time at which the current is drawn. Alternatively, the battery charge level monitor 301 may be a voltage sensor operable to read the voltage level of the battery unit 302. If the voltage of the battery unit 302 falls outside of a prescribed range, the battery charge level monitor 301 may communicate this event to the charge management controller 305 to instruct the charge management controller 305 to recharge the battery unit 302. For example, the battery charge level monitor 301 may communicate the event to the charge management controller 305 when the voltage of the battery unit 302 falls below about 95%, 96%, 97% or 99% of its charging capacity. Any off the shelf algorithm may be used to measure voltage, temperature, and battery life to provide a "state of charge" estimate.

In at least one embodiment, the charge management controller 305 can be connected to an external power source 310 which may be an external device, such as the electronic device 12, that can provide power, but this might be optional in certain embodiments. The external power source 310 includes a battery unit 311 that may be used to recharge the battery unit 302 to maintain the voltage of the battery unit 302 in the prescribed range, as described above, and may act as a continuous source of supply voltage for the battery unit 302. In at least one alternative embodiment where more than one battery is used in the battery unit 302, the battery charge level monitor 301 may alternatively, or in addition thereto, be adapted to instruct the charge management controller 305 to recharge a first battery in the battery unit 302 using a second battery in the battery unit 302 before drawing power from the external power source 310. Alternatively, a super capacitor may be used to recharge the battery unit 302. In some cases, the charge management controller 305 and the battery charge level monitor 301 may be implemented using the same controller.

The voltage regulator stage 303 may include a plurality of voltage regulators and is generally used to regulate the voltage of the battery unit 302 to minimize instantaneous voltage sag caused by the internal resistance of the battery unit 302. The voltage regulator stage 303 may maintain the voltage of the battery unit 302 to within about 50 mV of the desired voltage, which may, for example, be about 2.8 V with a voltage ripple of less than about 1%. A first voltage regulator may be connected to the battery unit 302 and the remaining voltage regulators may be connected in series, causing each of the voltage regulators to limit the changes on the input voltage of subsequent voltage regulators.

The current regulator stage 304 can measure and monitor the drive current signals provided by the drive circuit 300d, which will correspond to the current flowing through one or more of the LEDs 22a-22N, such as through a pair of LEDs for example. For example, the current can vary based on the wavelength of light emitted by a given LED such as, but not limited to, between about 0.50 Amps for a 630 nm LED and 2 Amps for an 880 nm LED. The current regulator stage 304 may monitor the current by obtaining a feedback signal from the LED drivers 307 or from the multiplexer 306. For example, to achieve the desired light output intensity, each pair of emitters may have a separate current sense resistor, since to provide the desired light output at unique wavelengths, the current flowing through each pair of LEDs may be selected to be different. The feedback signal can be obtained using a low resistance sense resistor electrically connected to the cathode of the LEDs to measure the flow of current in the LEDs. In response to the feedback signal, the current regulator stage 304 may increase or decrease the bias voltage of each of the LEDs. For example, if the output illumination needs to be increased for a given LED, this is reflected in the feedback signal for the given LED and the current to the given LED will be increased to increase the output light from the given LED.

The multiplexer unit 306 can be used by the controller circuit 320 to control the operation of the LED drivers 307. For example, in at least one embodiment, the multiplexer unit 306 can include a first multiplexer connected to the anode of each the LED drivers and a second multiplexer connected to the sense resistors described above, located at the cathode of each of the LEDs. The first and second multiplexers have a sufficient number of channels (e.g., N channels) in order to select and provide control signals to control the output illumination that is collectively provided by the selected LEDs and may also preferably have a low interchannel resistance (e.g., less than about several Ohms) to minimize the impact of the multiplexers on the voltage and current sense of the drive circuit 300d.

Regulating the voltage and current of the drive circuit 300d can allow the intensity (e.g., illumination) of the light signals emitted by the LEDs 21a-21N of the light source unit 22 to be controlled such that the illumination light intensity is standardized, which can increase the quality of the images captured by the portable multispectral imaging device 10.

The controller circuit 320 is operable to determine the required driving intensity of the LEDs 21a-21N and to control the LED drivers 307 to cause the LEDs 21a-21N to emit the required light signal intensity. The controller circuit 320 can be mounted on the printed circuit board of the light source unit 22 and can be soldered onto a heat transfer pad to allow it to monitor temperature at the LEDs 21a-21N.

The controller circuit 320 includes a controller or microprocessor 322, memory (not shown) and a temperature sensor 321 in communication with the controller 322. Temperature sensor 321 may be any type of temperature sensor, including, but not limited to a thermistor or an optical sensor. Controller 322 may be implemented using the same controller that is used to implement the charge management controller 305 and/or the battery charge level monitor 301. The controller 322 can determine the driving intensity correction factor for each LED according to the techniques described herein. The controller circuit is operably coupled to the drive circuit 300d to provide the driving intensity correction factors to the drive circuit 300d to compensate the amplitude of the drive current signals so that the LEDs 21a-21N ultimately collectively provide the standardized light intensity output.

It has been found that there exists a sigmoidal relationship between pulse width modulated light output intensity and the measured reflectance, defined by the following equation:

$$S(x) = \frac{1}{1 + e^{-x}} \tag{1}$$

where x represents the pulse width modulated intensity and S(x) the reflected signal intensity.

Referring now to FIGS. 4A-4F, shown therein are graphical examples 410, 420, 430, 440, 450, 460 of the relationship between pulse width modulated output light intensity and actual reflectance showing this sigmoidal relationship, which may be obtained using an embodiment of the portable multispectral imaging device described herein. Each of the plots show reflectance as a function of intensity for a different wavelength. Example plots 410, 420, 430, 440, 450 and 460 show reflectance as a function of intensity for an LED emitting a light signal having a wavelength of 700 nm, 880 nm, 620 nm, 980 nm, 630 nm and 810 nm, respectively.

As shown in plot 410, the curve shown in the plot can be divided into three segments representing different states including: a first state 400 corresponding to a pre-firing state where the reflected signal is not significantly affected by the pulse width modulated intensity; a second region 401 where reflectance increases as pulse width modulated intensity increases; and a third region 402 corresponding to a plateau where increases in pulse width modulated intensity do not necessarily result in increases in reflectance. The third region 402 corresponds to the region in which the LEDs 22a to 22N of the portable imaging device 10 most often operate. However, in at least one embodiment, when driving the LEDs in this region the output light intensity for one or more of the LEDs 21a-21N may need to be modulated due to environmental constraints in order to provide a standardized, repeatable, illumination output. It should be understood that the term standardized light intensity output means that the light intensity output of the LEDs 21a-21N are fairly similar when there are changes in environmental conditions such as one or more of temperature, voltage and current based on calibration that can be done, as described below, so that correction factors can be applied to the control signals for the LEDs 21a-21N to reduce any changes in light intensity output that would otherwise result from the changes in the environmental conditions. Accordingly, the amount of modulation that may be used may be determined by calibration and periodically checked during the operation of the portable multispectral imaging device.

Figure 5:
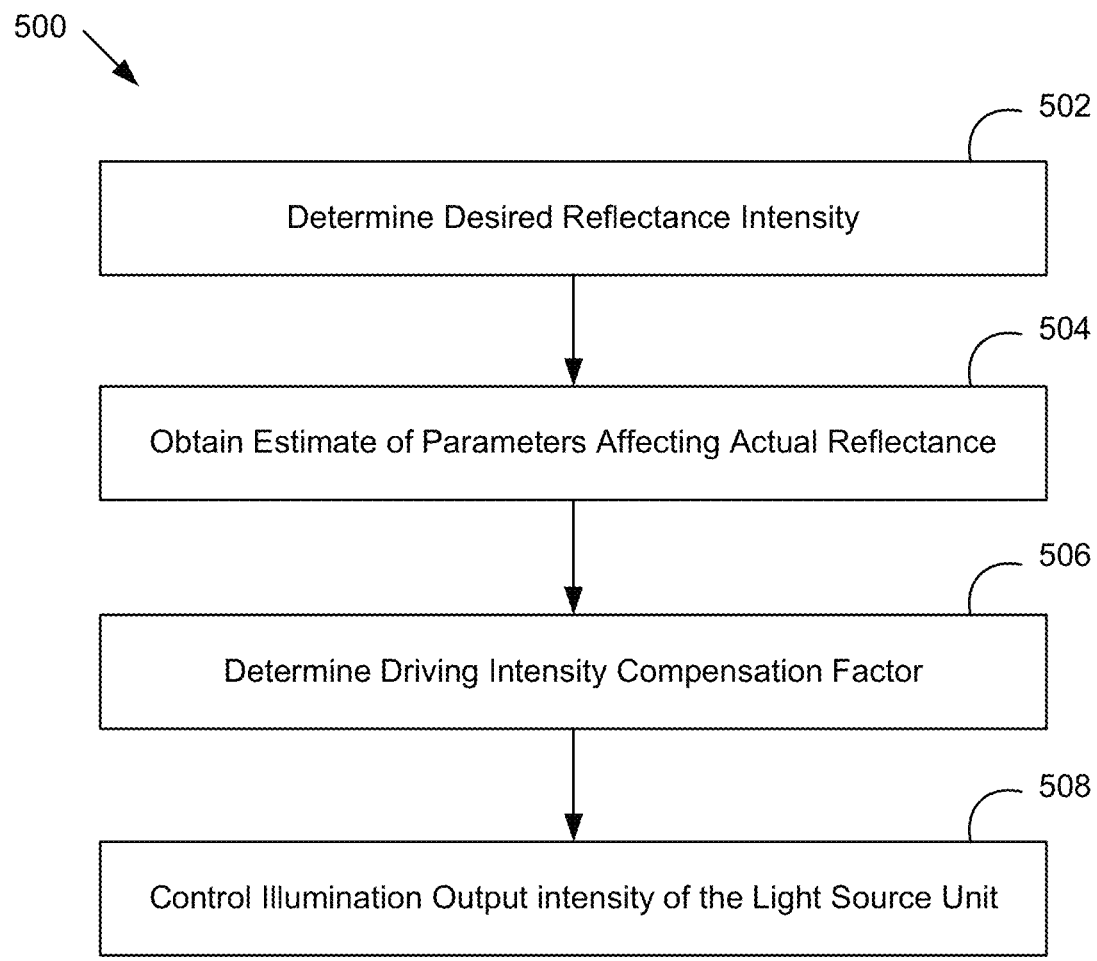
FIG. 5 is a flowchart of an example embodiment of a method for calibrating and standardizing illumination output intensity the portable imaging device of FIG. 1.
Figure 6A:
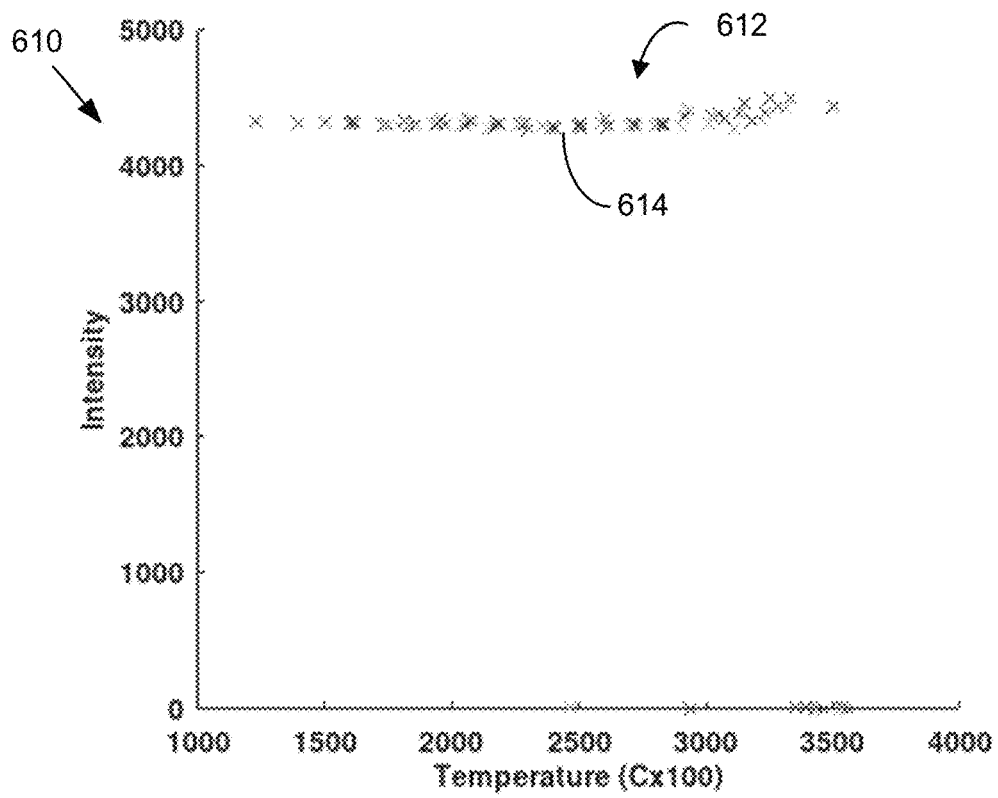
FIGS. 6A-6F show graphical examples of illumination output intensity over a range of temperatures for an example embodiment of the portable imaging device of FIG. 1.
Figure 6B:
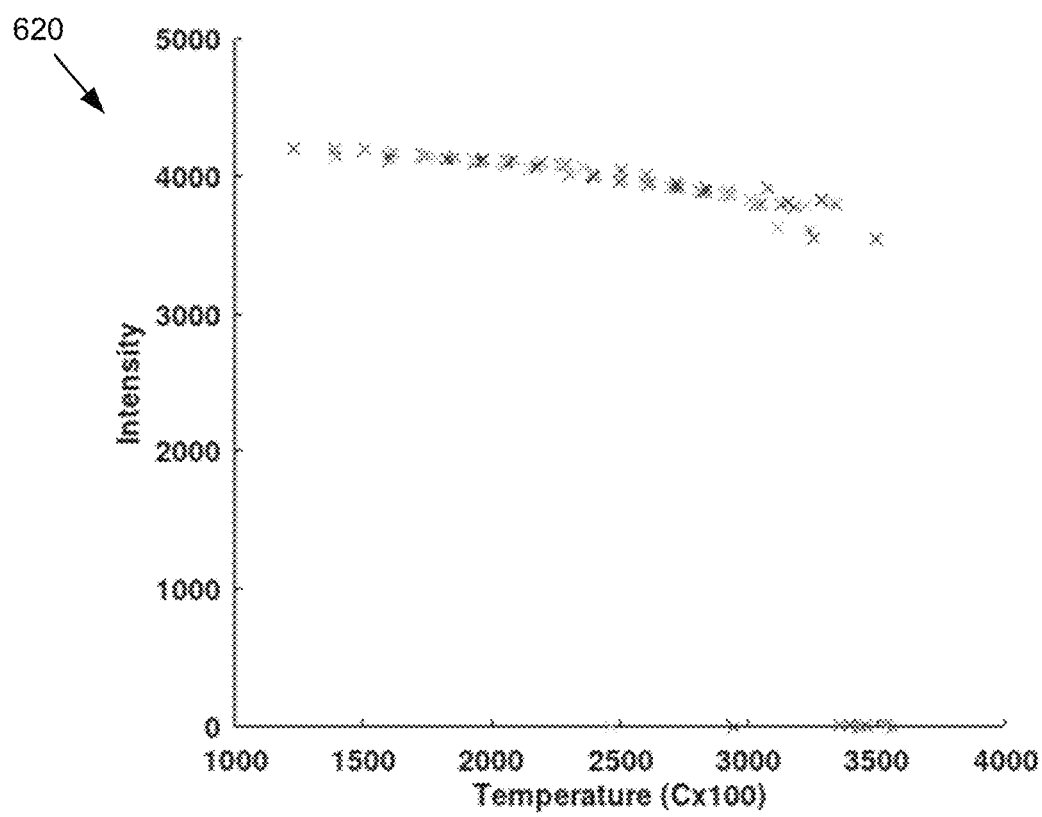
Figure 6C:
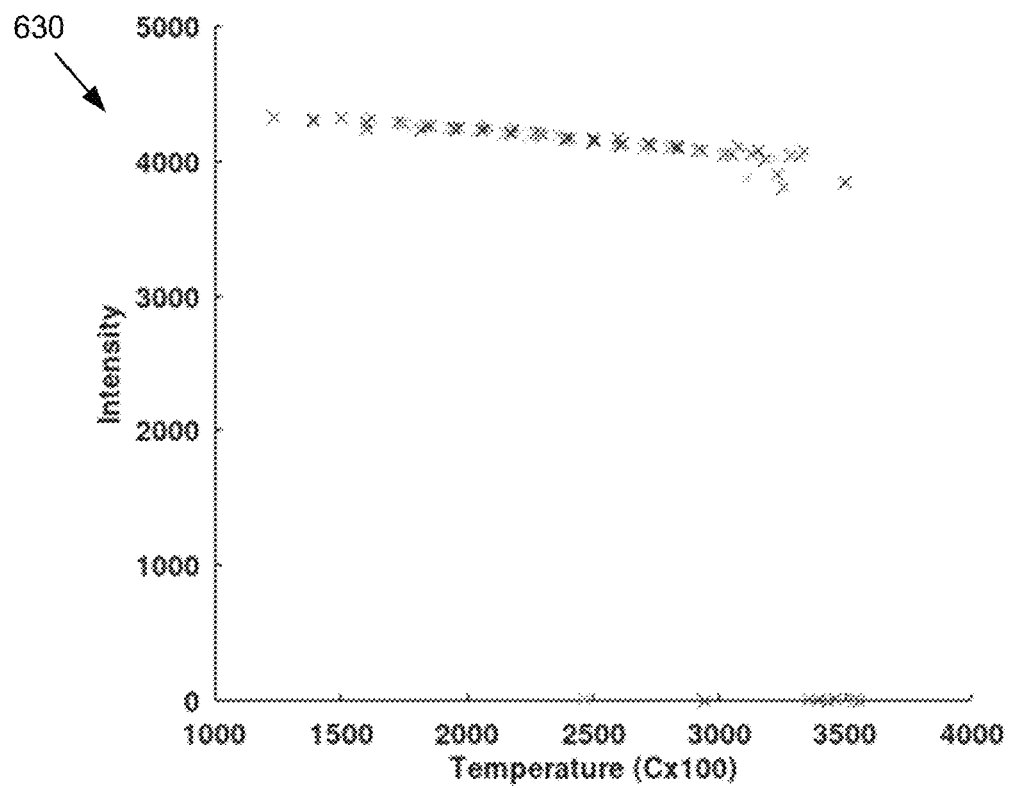
Figure 6D:
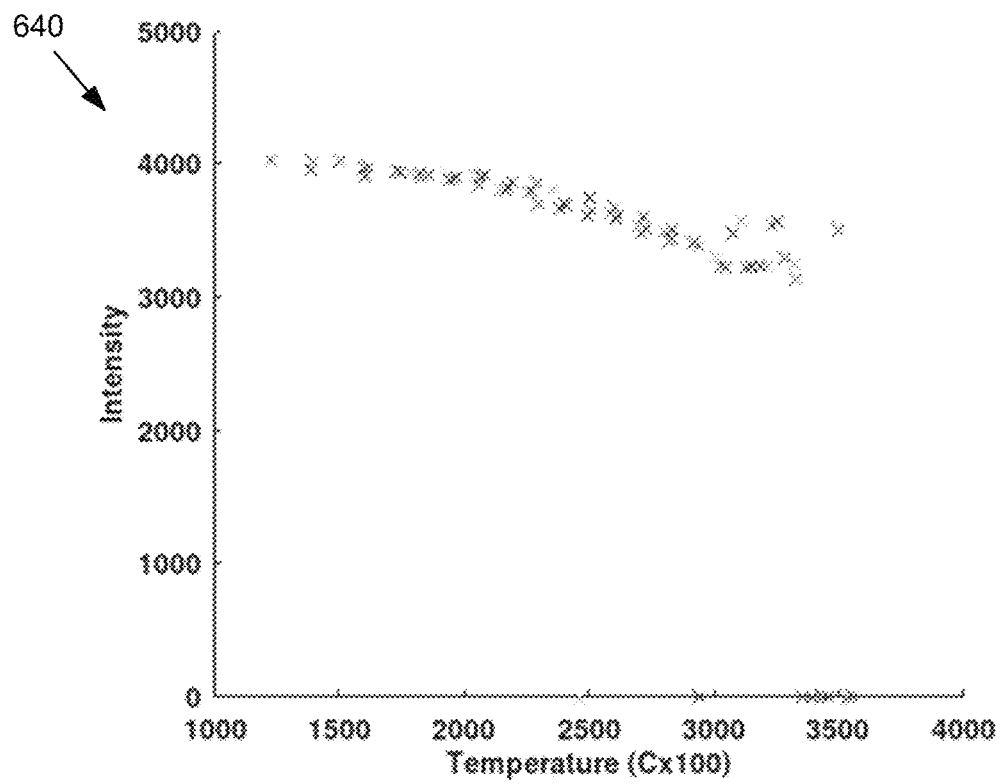
Figure 6E:
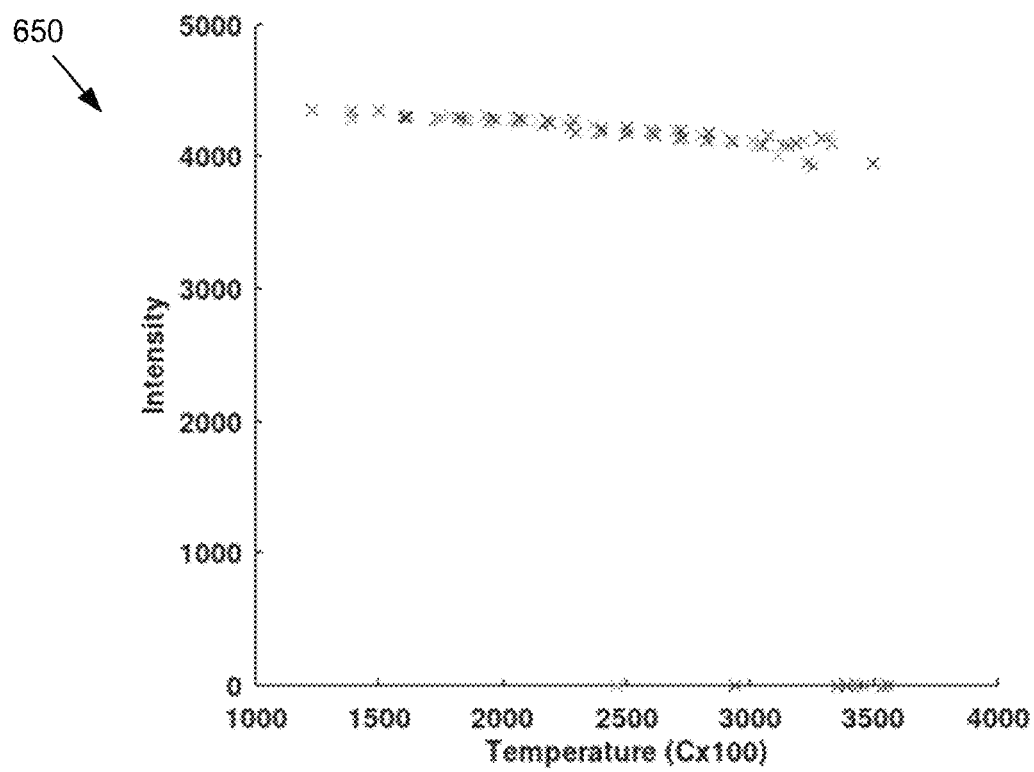
Figure 6F:
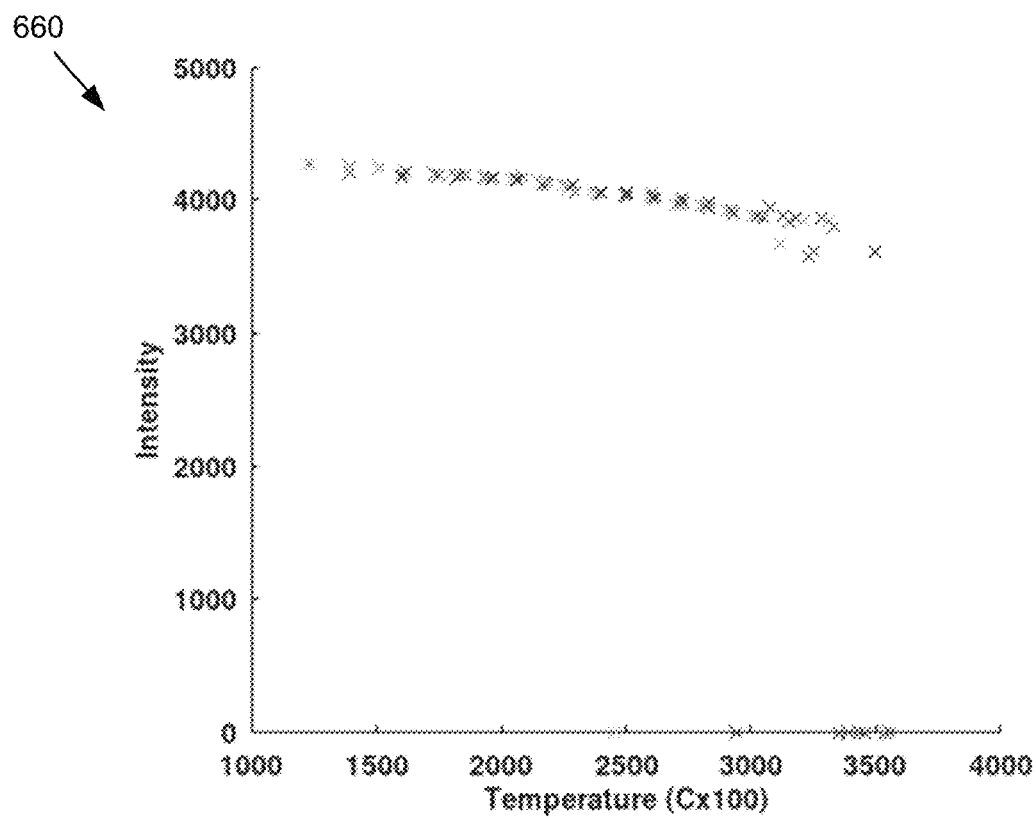

Referring now to FIG. 5, shown therein is a flowchart of an example embodiment of a method 500 for calibrating and standardizing light illumination intensity produced by the imaging device 10 to account for changes in environmental conditions. Due to the presence of various components in the portable multispectral imaging device 10, the output LED intensity and actual light reflectance intensity may differ, causing the actual light reflectance intensity to differ from the expected light reflectance. For example, one or more parameters including the internal resistance of the battery unit 302, the voltage sag experienced by the drive circuit 300d, the LED junction temperature and/or component value drift can affect the magnitude of the light signal output produced by the light source unit 22. If the output intensity is not corrected to account for variations in these parameters, then the actual reflectance of the light signals emitted by the LEDs 22a to 22N may fall outside an acceptable range of light reflectances, which may compromise the accuracy of the tissue assessment that is performed on the acquired images. Accordingly, to obtain the expected light reflectance, it may be necessary to apply a correction factor to the light source unit 22.

The relationship between the reflectance intensity and light output intensity where the light output is provided to an ROI may be defined, to a first order by ignoring backscatter, by the following equation:

$$R(x,y,L)=\alpha(x,y,L)I(x,y,d,V,C,T) \qquad (2)$$

where R is the reflectance intensity, I is the output intensity and α is the reflectance coefficient of the ROI. The reflectance intensity varies over the space (x, y) and varies as a function of wavelength L. The reflectance coefficient α also varies over the space (x, y) and varies for each LED wavelength L. The intensity I is a function of (x, y) and additionally of the distance between the LED and the surface that is illuminated at the ROI, the voltage provided to the corresponding LED drivers 307, the current flowing through the LED and the temperature at the junction of the LED. Equation 2 may be defined for each LED of the light source unit 22. By tightly controlling the four variables of d, V, C and T, one can obtain an estimate of the reflectance.

As shown by equation 2, variations in the output intensity I affect the measured reflectance R and therefore may compromise the accuracy of the tissue assessment performed on the acquired images. In at least one embodiment, the method 500 may be used to correct the output intensity to account for variations in the parameters described above. For example, the method 500 may provide a correction to the drive current signals which is ultimately reflected in the LED control signals so that the output intensity of each LED results in a reflectance intensity is within a certain amount of the expected reflectance, such as, but not limited to, within about 5%, for example.

The method 500 may be performed using a processor that is in electrical communication with the emitter circuitry 300. The method 500 is used to calibrate the portable multispectral imaging device 10 without requiring a reference measurement in the field of view of the portable multispectral imaging device 10. To calibrate the imaging device 10, the user may aim the imaging device 22 at a ROI on a tissue surface and trigger the image capturing activity. For example, the user may interact with the electronic device 12 which may run a software program, such as the image acquisition module 48, to allow the user to provide control signals to the portable multispectral imaging device 10 to cause it to emit light signals and perform image capture.

Accordingly at step 502, the method 500 involves determining a target light intensity for each LED while the portable multispectral imaging device 10 is emitting light in response to the aforementioned user control. The target light intensity for each LED may be different from one another to compensate for different environmental and collectively contribute to a standardized output illumination for the whole light unit so that the resulting light reflectance from the ROI that is detected is within an acceptable range of a desired reflectance intensity that is sufficient to accurately perform tissue assessment. Once the desired reflectance intensity is known, in future usages of the method 500, step 502 may involve reading the desired light reflectance intensity from a data store in memory.

At step 504, the method 500 involves obtaining estimates of parameters that affect light output intensity for each LED. These parameters may be used to determine changes in environmental conditions for each LED. For example, in at least one embodiment obtaining estimates of parameters that affect light output intensity may include obtaining estimates of the temperature of the light source unit 22, when the voltage and current that is provided to the LED drivers 307 of the light source unit 22 are held constant.

In at least one embodiment, obtaining estimates of parameters that affect light output intensity may involve obtaining estimates of the voltage and current of the light source unit 22. An estimate of the voltage can, for example, be obtained from a voltage regulator that is part of the voltage regulator stage 303. Similarly, an estimate of the current can be obtained by using a current regulator in the current regulator stage 304.

Determining the temperature may involve determining the junction temperature of the array of LEDs 21a-21N. For example, the temperature may be measured on a ground plane to which the LEDs 21a-21N are connected, such as the board 202b. Alternatively, the temperature may be measured at the junction of each of the LEDs 21a-21N which may all be provided as inputs to the microprocessor 322. Accordingly, in at least some embodiments, the voltage and current provided to the LED drivers 307 may be held constant, while junction temperature of the array of LEDs may vary.

In accordance with the teachings herein, obtaining an estimate of parameter values that may affect the light output intensity of the LED unit 22 may include measuring a) one of temperature, voltage and current as described previously, b) two of temperature, voltage and current as described previously, or c) all three of temperature, voltage and current as described previously. The latter option may provide the more accurate calibration result while the other options may be done to perform an approximate calibration more quickly.

At step 506, the method 500 involves determining a driving intensity correction factor based on the parameters values that were measured at step 504. For example, the environmental condition(s) (e.g., current, voltage and temperature) are first measured. Then, for example, the driving intensity correction factor may be determined with reference to a look-up table stored in memory where the measured parameter values may be used as inputs into the look-up table. This can be repeated for each LED to determine the driving intensity correction factor by which the drive current to each LED may be altered so that the output of each LED is the target light intensity described earlier. Alternatively, the correction factor driving intensity may be determined by using one or more correction curves or using a polynomial that is defined over an output intensity range for each LED.

Referring now to FIGS. 6A-6F, shown therein are graphical examples 610, 620, 630, 640, 650 and 660 showing the nearly linear relationship between temperature and the pulse width modulated intensity required to achieve a known light output, for a constant voltage and current. For example, graphical example 610 shows data points 612 corresponding to measurements of intensity for various temperatures and line 614 corresponds to a best fit line. Each of graphs 610, 620, 630, 640, 650, and 660 correspond to graphical examples of temperatures as a function of pulse width modulated intensity for wavelengths of 700 nm, 880 nm, 620 nm, 980 nm, 630 nm and 810 nm, respectively. As can be seen in FIGS. 6A-6F, for a target reflection intensity, which in a test environment can be equated to a target emission intensity (i.e., a target light output), a relationship between the measured temperature, and driving intensity can be obtained. This allows for the calculation of a correct driving intensity correction factor for a given junction temperature to compensate for changes in one or more environmental conditions and allow for the appropriate light output. This may, in one instance, be corrected to a first order. Additionally, in at least one embodiment, higher order polynomial fits may also be performed to this relationship to include non-linear terms. However, this may be dependent on how closely the measured temperature is reflective of the actual junction temperature.

Referring back to FIG. 5, at step 508, now that the driving intensity correction factors have been determined for each LED, the method 500 involves controlling the LEDs according to the corresponding correction factor that has been determined based on the measured parameter values to obtain the target light intensity output. For example, based on the calibration that is done, an example of which is shown in FIGS. 6A-6F, a linear relationship may be derived between temperature and actual output intensity which can then be used to determine the corresponding correction factor. This may also be performed for determining corrections factors for voltage and current variations. Accordingly, in at least one embodiment, controlling the LEDs 22a to 22N involves separately controlling the intensity of each of the LEDs in the array of LEDs. As shown in FIGS. 6A-6F, the relationship between intensity and temperature can differ at different wavelengths. Accordingly, each of LEDs 22a to 22N may be provided with a different control signal so that the LEDs 22a to 22N may generate light at different intensities such that the reflectance data that is measured is within an acceptable range.

Once the light source unit 22 is calibrated, the portable multispectral imaging device 10 can be used to capture images of the ROI of the tissue surface that is being monitored and the captured image data can subsequently be processed to provide a tissue assessment. For example, the captured images may be processed using spectral unmixing algorithms to generate a color map as described in PCT Application Publication No. WO 2018/035612 filed on Aug. 24, 2017. The images may be processed by the electronic device 12. Alternatively, in at least one embodiment, the images may be processed by the portable multispectral imaging device 10. The color map may be displayed to the user via the display of the electronic device 12.

Referring now to FIGS. 7A-7F, shown therein are graphical examples of plots 710, 720, 730, 740, 750 and 760 of reflectance over a range of temperatures once the calibration method 500 is applied. In plot 710, lines/regions 712a and 712b correspond to the upper and lower limits, respectively, of acceptable reflectances, that may correspond to reflectances that are suitable for obtaining images with an acceptable signal to noise ratio that allows for accurate tissue assessment to be performed. Data points 714 (shown as x's) correspond to measured reflectances obtained at different temperatures. Line 716 corresponds to a mean of the measured reflectances and line 718 corresponds to a line of best fit representing a trend in the data. In some cases, line 718 may be used to apply a second order correction. For example, a second linear regression could be calculated based on the difference between the data points 714 and the first fit slope 718. The two corrections could then be applied sequentially to correct for the difference between the calculation and the desired output. Higher order corrections may also subsequently be applied, in the same manner. The lines 716 and 718 may be referred to as correction curves.

Each of plots 710, 720, 730, 740, 750, 760 correspond to reflectance data obtained when the tissue region is illuminated by an LED having a different wavelength. Plots 710, 720, 730, 740, 750, 760 correspond to light sources having wavelengths 700 nm, 880 nm, 620 nm, 980 nm, 630 nm and 810 nm, respectively. As shown, applying the correction factor allows the resulting reflectance to remain within an acceptable range of reflectances across a variety of temperatures for the LEDs.

Figure 8:
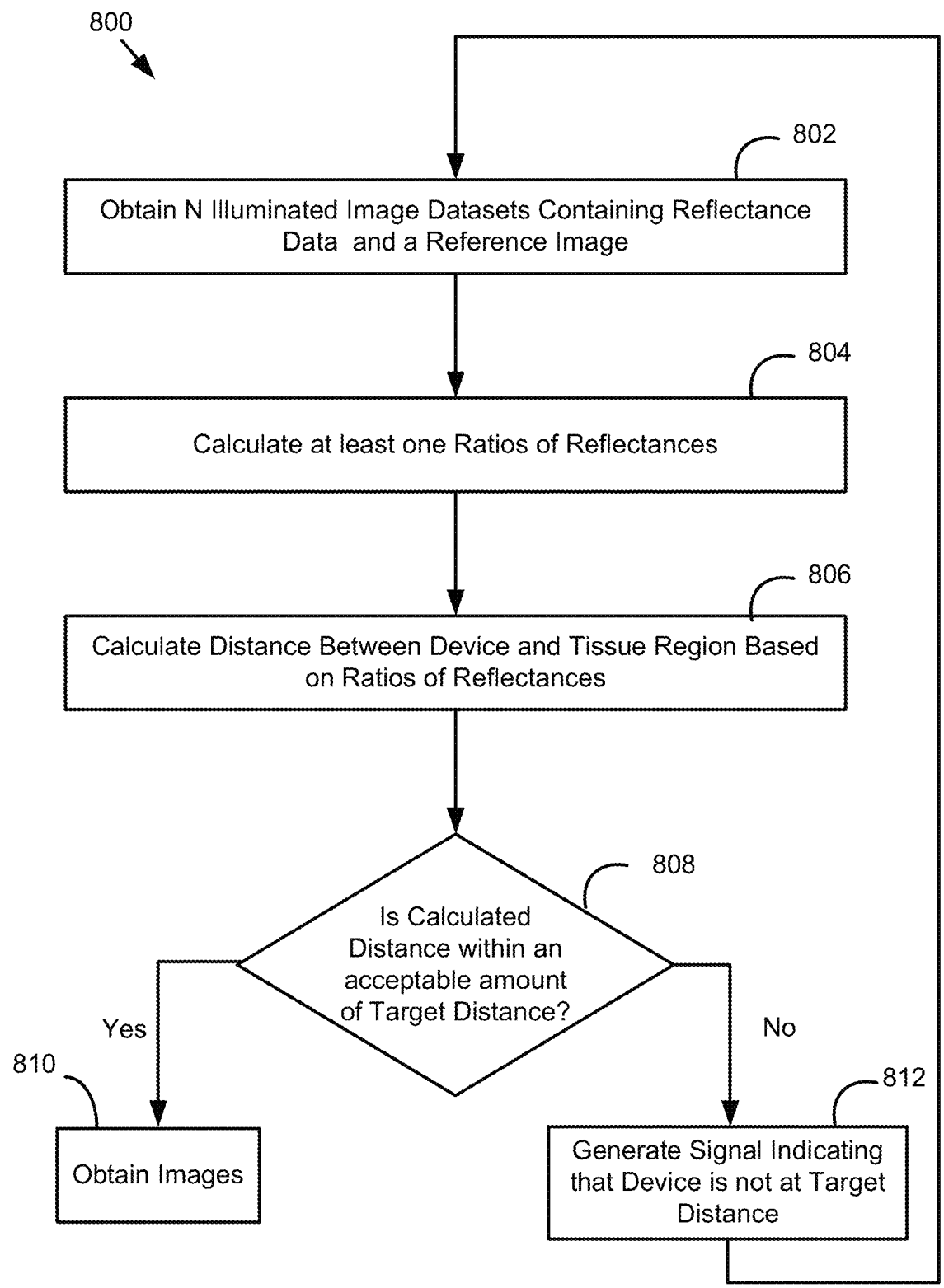
FIG. 8 is a flowchart of an example embodiment of a method for positioning the portable imaging device of FIG. 1 with respect to a surface that is being imaged for obtaining images with improved image quality.

Referring now to FIG. 8, shown therein is a flowchart of an example embodiment of a method 800 for positioning the portable multispectral imaging device 10 when images are being acquired for obtaining images with improved multi-spectral unmixing accuracy. Method 800 may be used separately, or in combination with method 500. Adequate positioning of the portable multispectral imaging device 10 relative to the tissue region of interest is important in obtaining accurate reflectance data. Due to imperfect lensing of the LED light sources, the light produced by the LEDs fall off differentially from the position of the LEDS on the light source unit 22, such that the reflected intensity measured at a particular distance is different for each LED, creating ideal imaging iso-surfaces. Iso-surfaces are non-planar surfaces for which the ratio of intensity between two LEDs is constant for a particular distance. When the portable multi-spectral imaging device 10 is adequately positioned, the target region is positioned on the iso-surface.

However, when the portable multispectral imaging device 10 is inadequately positioned, the ROI on the tissue surface may be positioned outside the iso surface. Deviation from the iso-surfaces modifies the ratio of light emitted by pairs of diametrically opposed LEDs reaching the ROI of the tissue surface, which may lead to inaccurate reflectance data, which may in turn compromise tissue assessment. Determining the distance between the surface of the LEDs 21a-21N of the portable multispectral imaging device 10 and the ROI of the tissue surface can aid in maintaining the portable multispectral imaging device 10 within a target distance range (and more preferably the imaging device 10 is maintained at a desired distance) of the ROI. The target distance is selected so that the ROI of the tissue surface is positioned on the iso surface. The term target distance range refers to an acceptable amount of variation, such as up to about +/−5%, up to about +/−10% or up to about +/−1 15%, for example, in the actual distance of the camera(s) of the imaging device 10 from the target distance. For example, when considering the ratio of two LEDs, if the output light from the LED's falls off monotonically, there exists a point in space for all of X & Y where the ratio of the two LEDs is a fixed number.

Distance is generally inversely proportional to the square of light intensity from a light source. However, due to imperfect lensing of light, light fall off may deviate from this relationship. Accordingly, to adequately determine the desired distance (i.e., a distance within the target distance range) between the LEDs of the portable multispectral imaging device 10 and the ROI of the tissue surface, adjusting the output intensity of the LEDs alone may not be sufficient and the device 10 may need to be repositioned. However, method 800 in FIG. 8 provides a technique for determining this desired distance. The method 800 may be performed using a processor of the portable multispectral imaging device 10 or a processor of the electronic device 12.

At step 802, the method 800 involves capturing N images, each of the N images being captured when the region of interest is illuminated by a light signal produced by one of the LEDs 21a-21N having a unique wavelength and then capturing a reference image when the region of interest is not illuminated by any of the LEDs 21a-21N. The reference image is used to obtain an estimate of the inherent noise within a captured image. This ambient noise can then be subtracted from the lit images. Therefore, a total of N+1 images are captured. Each of the images contain measurements of the reflectance of the ROI. The parameter N is an integer and may be at least 2. Each of the captured images contain reflectance data. To capture these N+1 images, the user may aim the portable multispectral imaging device 10 at the ROI on the tissue surface. To assist the user in positioning the portable multispectral imaging device 10, the display of the electronic device 12 may for example display a positioning indicator overlaid onto a real-time feed of "ambient light" images of the ROI that are captured by the portable multispectral imaging device 10. For example, the positioning indicator may be a reticle such as a crosshair in the center of the display. Using the positioning indicator, the user may position the imaging device 10 such that the reticle is aligned with the center of the region of interest on the tissue surface.

The image acquisition module 48 may include software instructions which when executed by a processor, result in the capture of images in rapid succession to avoid motion of the subject and/or motion of the portable multispectral imaging device 10, which may be processed to produce more accurate tissue assessment results. For example, as described previously, the image acquisition module 48 includes software instructions that is used to configure the portable multispectral imaging device to capture images in a time period of approximately 16 ms to 70 ms per image. Alternatively, the software instructions for performing image capture may be stored on the portable imaging device 10 and executed by the controller 20 to implement image capture in near real-time.

At step 804, the method 800 involves obtaining the measure of reflectance from the acquired at step 802 and then calculating ratios of these measured reflectances. For example, an individual image is acquired during the illumination period of each LED for the ROI. The reflectance may be measured for the entire image or for a subset of the pixels of the acquired images where the subset of pixels represents a "distance" point. For example, the central 20 pixels in an acquired image may be selected to act as a "distance" point. Each of the ratios can be calculated by dividing these measured reflectances for LEDs that are located in a diametrically opposed fashion. At least one ratio between two reflectances is calculated At step 806, the method 800 involves determining the distance between the device and the tissue region (i.e., ROI on the tissue surface) based on the ratios calculated at step 804. For example, each of the calculated ratios can be compared with known data about the relationship between the ratio of reflectances and distance for a given wavelength. As shown in FIGS. 9A-9D, which will be described in further detail below, there exists a linear relationship between ratios of reflectances and distance for a given wavelength. By comparing the calculated ratios with the known data, the distance between the LEDs 21a-21N used to obtain the calculated ratios and the tissue surface of the ROI can be determined. For example, in the case of M>2, fitting can be performed in multiple dimensions to get the correct distance.

In some cases, a temporal filter such as a finite impulse response filter may be applied to the calculated distances to minimize the effect of noise.

At step 808, the method 800 involves determining if the calculated distance at step 806 is within the target distance range. The target distance range can correspond to a range that includes a target distance, for example, a distance for which the ROI is positioned on an ideal iso-surface as described earlier and for which the light source unit has been calibrated to return a known reflectance for a known target. The target distance range may also correspond to a range of distances for which the portable multispectral imaging device is calibrated and for which parameters of interest can be calculated. If the calculated distance is within the target distance range, the method 800 proceeds to step 810. If the calculated distance is not within the target distance range, such as within about 5%, about 10% or about 15% of a target distance, the method 800 proceeds to step 812.

At step 810, the method 800 involves capturing images that are then processed and analyzed for performing tissue assessment when the imaging device 10 is within the target distance range to the ROI on the tissue surface being imaged. For example, N images may be captured, where each of the N images are captured when the tissue region is illuminated with a light signal having a different wavelength. In addition, a reference image when the tissue region is not illuminated may be captured. The images may be automatically captured without user input. For example, an initial image acquired by the portable multispectral imaging device 10 may be compared with one or more template images stored in memory and the subsequent images may be auto-captured when the initial image acquired by the imaging device 10 meets predefined criteria of similarity with at last one of the template images. At step 810, the method 800 may also involve displaying feedback to the user on the display of the electronic device 12 to indicate that the portable multispectral imaging device 10 is within the target distance range of the ROI and images have been captured. Captured images may then be processed and analyzed to perform tissue assessment.

If the imaging device 10 is not within the target distance range, then at step 812 the method 800 involves generating a signal to indicate that the distance between the LEDs 21a-21N and the ROI is not within the target distance range. The signal can provide feedback to the user to allow the user to reposition the imaging device 10 so that it is closer to the target distance (i.e., within the target distance range). For example, the display of the electronic device 12 may be used to display a visual alert that the portable multispectral imaging device 10 is too close or too far from the ROI of a tissue surface and instruct the user to move the portable multispectral imaging device 10 in a certain direction by a certain amount so that the LEDs 21a-21N are within the target distance range relative to the ROI on the tissue surface. Alternatively, or in addition thereto, some of the software instructions in the imaging acquisition module 48 may cause the electronic device 12 to generate auditive cues to instruct the user to move the portable multispectral imaging device in the correct direction that will cause the surface of the ROI to be positioned on an ideal iso-surface. The method 800 then returns to step 802 and a new set of images is captured to determine whether the distance between the LEDs 21a-21N and the ROI is within the target distance range. The method 800 may be repeated until the portable imaging device 10 is at or within an the target distance range.

Referring now to FIGS. 9A-9D, shown therein are graphical examples of plots 910, 920, 930 and 940 of distance as a function of reflectance ratios between light signals of known wavelength, showing a linear relationship between distance and ratios of reflectance, where $R^2$ is the correlation coefficient. For example, plot 910 shows data points 911 that correspond to various measurements of distance at different ratios of measured reflectance between two light sources of known wavelength. Line 912 is a line of best fit that can be used to calculate the distance between the imaging device 10 and the ROI, as described at step 808. Plots 920, 930, 940 show similar data points and best fit lines that correspond to measured distance for ratios between light sources having different known wavelengths. The LEDs that generate the highest correlation ($R^2$) with the largest slope may be selected for performing these calculations as these LEDs essentially give us the greatest sensitivity to measuring distance. Using these known linear relationships and the ratios calculated at step 804 of method 800, the distance between the imaging device and the tissue region can be estimated. For example, when the distance is determined for 2 pairs of LEDs, this produces a line in 2D space, when the distance is determined for 3 pairs of LEDs, this produces a line in 3D space and when it is determined for N pairs of LEDs, this produces a line in N dimensional space. Moving to fitting the line in high order space may improve the accuracy but a suitable estimate of the distance may be determined for one pair of LEDs.

Figure 10:
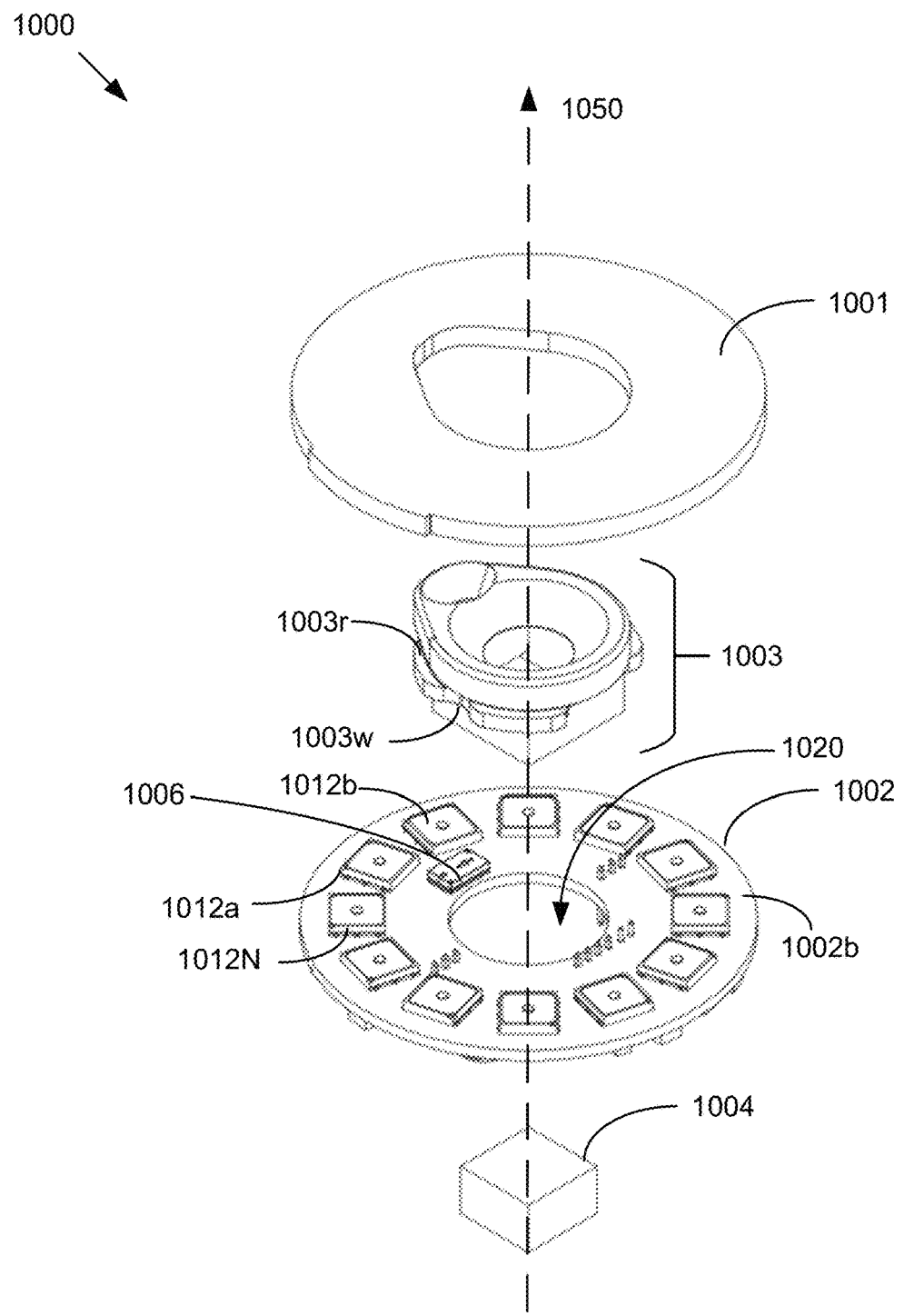
FIG. 10 is an exploded view of some components of another example embodiment of the portable imaging device.

Referring now to FIG. 10, shown therein is an exploded view of an example embodiment of optical hardware 1000 that may be used by the portable multispectral imaging device 10. The optical hardware 1000 may be substantially similar to the optical hardware 200 but additionally includes a distance sensor 1006. Similar to the optical hardware 200, the optical hardware 1000 includes a light sensor (e.g., a camera) 1004 and a light source unit 1002, including LEDs 1012a-1012N placed around an aperture 1020, a light shield 1003, which includes an annular rib portion 1003r and a hollow walled portion 1003w, and a diffusing element 1001 (e.g., a diffuser). The light sensor 1004, the light source unit 1002, the shield 1003 and the diffusing element 1001 can be disposed in a concentric fashion relative to one another about a common central axis 1050. In at least one embodiment, the diffuser 1001 may be optional if a lens that can perform similar functions is incorporated in its place. The optical hardware 1000 can be connected to a circuit board, on which a processing unit can be mounted (not shown).

The distance sensor 1006 may be part of the light source unit 1002. For example, the distance sensor 1006 may be placed and connected to the printed circuit board 1002b of the light source unit 1002 as shown. The distance sensor 1006 may be positioned such that the field of view of the distance sensor 106 substantially overlaps with the field of view of the light sensor 1004. Positioning the distance sensor 1006 in this manner allows for the distance between the light sensor 1004 and the surface of the ROI to be approximated by the distance sensor 1006. The distance sensor 1006 may be any type of sensor capable of measuring distance, including, but not limited to a time-of-flight sensor such as, but not limited to, a light detection and ranging (LIDAR) sensor, for example.

For example, the distance sensor 1006 may be a sensor unit which includes a light source that can emit one or more pulses of light, a light detector that can detect reflected light when the one or more pulses of light interact with the surface of an object and a processor that can calculate the time taken for an emitted pulse of light to be reflected from the surface of an object back to the sensor (e.g., the VL53L4CX time-of-flight sensor by STMicroelectronics).

Referring now to FIG. 11, shown therein is an exploded view of another example embodiment including optical hardware 1100 and a circuit board 1108 that may be used by the portable multispectral imaging device 10. The optical hardware 1100 may be substantially similar to the optical hardware 1000. However, in contrast to light source unit 1002, light source unit 1102 may have the shape of an open circle. The open portion of the light source unit 1102 can be sized to accommodate a camera 1110, as will be described below.

Similar to the optical hardware 1000, the optical hardware 1100 includes a light sensor (e.g., a camera) 1104 and a light source unit 1102, including LEDs 1112a-1112N placed around an aperture 1120, and a diffusing element 1101 (e.g., a diffuser). Although not shown, optical hardware 1100 may include a light shield, similar to optical hardware 1000. The light sensor 1104, the light source unit 1102, and the diffusing element 1101 can be disposed in a concentric fashion relative to one another about a common central axis 1150.

The light source unit 1102 and the light sensor 1104 may be connected to circuit board 1108 which includes a processing unit which can control the operation of the portable multispectral imaging device. The processing unit can include the controller 20. The circuit board 1108 may include a camera 1110 such as a thermal infrared camera for measuring temperature, for example. For example, in some cases, images obtained by the portable multispectral imaging device can include images captured by the camera 1110, for example, a temperature map (e.g., a two-dimensional map). When the optical hardware 1100 is assembled with the circuit board 1108, the camera 1110 is adjacent to the light sensor 1104 and to the LEDs of the light source unit 1102. The open portion of the light source unit 1102 allows the camera 1110 and the light sensor 1104 to be positioned in close proximity, such that the field of view of the light sensor 1104 and the camera 1110 substantially overlap.

Figure 12:
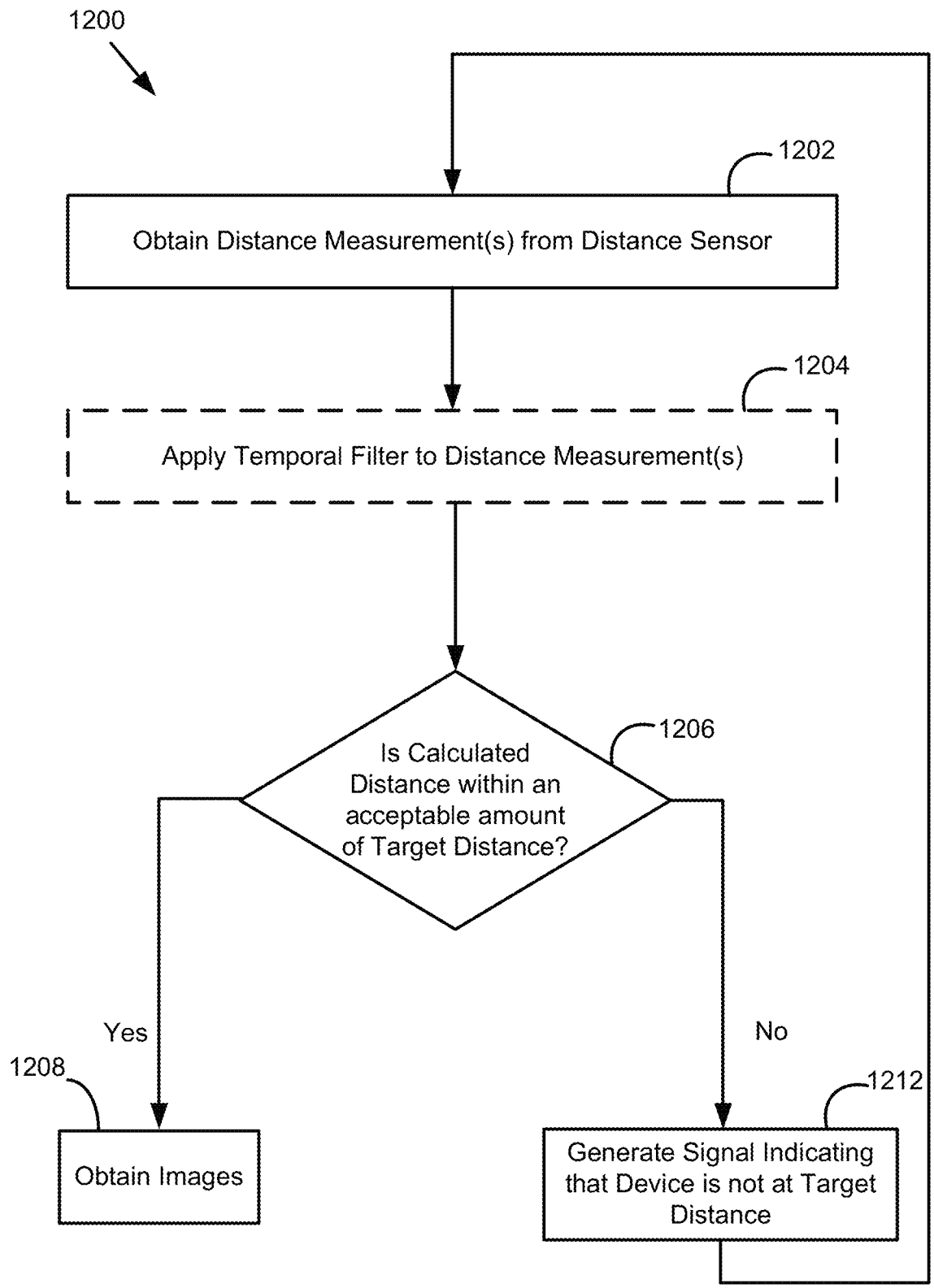
FIG. 12 is a flowchart of an example embodiment of a method for positioning the portable imaging device of FIGS. 10-11 with respect to a surface that is being imaged for obtaining images with improved image quality.

Referring now to FIG. 12, shown therein is a flowchart of an example embodiment of another method 1200 for positioning the portable multispectral imaging device 10 in order to obtain images that result in improved multispectral unmixing accuracy. Method 1200 may be implemented in combination with the optical hardware 1000 or optical hardware 1100. Similar to method 800, method 1200 may be used separately, or in combination with method 500. Method 1200 may be used as an alternative to method 800. For the same time period, when compared to method 800, method 1200 can obtain a greater number of measurements of distance and accordingly provide a more precise measure of distance between the portable multispectral imaging device 10 and the surface of the ROI. Since method 1200 involves the use of a distance sensor, such as distance sensor 1006, distance measurements can be obtained at a higher rate than in method 800, since the distance sensor is not limited by a frame rate, unlike the light sensor 204 (e.g., camera) used in method 800.

At step 1202, the method 1200 involves using a distance sensor to obtain distance measurement(s) of the distance between the portable multispectral imaging device 10 and the surface of the ROI from the distance sensor. As described with reference to FIG. 10, the distance between the portable multispectral imaging device 10 and the surface of the ROI may be approximated by the distance sensor by positioning the distance sensor such that the field of view of the distance sensor substantially overlaps with the field of the view of the light sensor of the portable multispectral imaging device 10. The user may aim the portable multispectral imaging device 10 at the ROI on the tissue surface. Similar to method 800, to assist the user in positioning the portable multispectral imaging device 10, the display of the electronic device 12 may for example display a positioning indicator overlaid onto a real-time feed of images of the ROI, such as "ambient light" images, that are captured by the portable multispectral imaging device 10. For example, the positioning indicator may be a reticle such as a crosshair in the center of the display. The location of the positioning indicator is determined based on the measurements obtained by the distance sensor as described below. Using the positioning indicator, the user may position the imaging device 10 such that the reticle is aligned with the center of the region of interest on the tissue surface.

At step 1204, the method 1200 involves applying a filter to the distance measurement(s) obtained at step 1202. Any type of filter that can minimize the effect of noise in the data received from the distance sensor (i.e., non-physiological movement noise) and determine an average distance from the distance measurement(s), may be used, including, but not limited to a temporal filter such as a finite impulse response (FIR) filter (e.g., a low pass FIR filter). For example, a FIR filter with approximately 5 to 20 filter taps may be used. The number of taps may depend on the rate at which the distance sensor can obtain distance measurements. Step 1204 may be optional in some cases. The filtering is helpful as the sensor returns (noisy) data at a much higher rate than physiological movement and filtering the data removes some of the non-physiological movement noise.

At step 1206, similar to step 808 of method 800, the method 1200 involves determining if the distance measured at step 1202 (or step 1204) is within a target distance range. The target distance range can correspond to a range from a target distance for which the ROI is positioned on an ideal iso-surface as described earlier with reference to FIG. 8 and for which the light source unit has been calibrated to return a known reflectance for a known target. The target distance range may correspond to a range of distances for which the portable multispectral imaging device is calibrated and for which parameters of interest can be calculated. If the calculated distance is within an acceptable amount of the target distance, such as within about +/-5%, about +/-10% or about +/-15%, that is, the calculated distance is within the target distance range, the method 1200 proceeds to step 1208. If the calculated distance is not within the target distance range, the method 800 proceeds to step 1210.

At step 1208, similar to step 810 of method 800, the method 1200 involves capturing images that are then processed and analyzed for performing tissue assessment when the imaging device 10 is within the target distance range to the ROI on the tissue surface being imaged. For example, N images may be captured, where each of the N images are captured when the tissue region is illuminated with a light signal having a different wavelength. In addition, a reference image when the tissue region is not illuminated may be captured. The images may be captured by the user or automatically captured without user input. For example, images may be auto-captured when the distance is determined to be within the target distance range. At step 1208, the method 1200 may also involve displaying feedback to the user on the display of the electronic device 12 to indicate that the portable multispectral imaging device 10 is within the target distance range of the ROI and images have been or should be captured. For example, feedback may be displayed in the form of a tape measure, as will be described in further detail with reference to FIGS. 13A-13B. Captured images may then be processed and analyzed to perform tissue assessment.

If the imaging device 10 is not within an acceptable amount of the target distance range, then at step 1210, similar to step 812 of method 800, method 1200 involves generating a signal to indicate that the distance between portable multispectral imaging device and the ROI is not within the target distance range. The signal can provide feedback to the user to allow the user to reposition the imaging device 10 so that it is closer to the target distance. For example, the display of the electronic device 12 may be used to display a visual alert that the portable multispectral imaging device 10 is too close or too far from the ROI of a tissue surface and instruct the user to move the portable multispectral imaging device 10 in a certain direction by a certain amount so that it is within the target distance range relative to the ROI on the tissue surface. Alternatively, or in addition thereto, some of the software instructions in the imaging acquisition module 48 may cause the electronic device 12 to generate auditory cues to instruct the user to move the portable multispectral imaging device in the correct direction that will cause the surface of the ROI to be positioned on an ideal iso-surface. The method 1200 then returns to step 1202 and new distance measurement(s) are obtained to determine whether the distance between the multispectral portable imaging device and the ROI is within an the target distance range. The method 1200 may be repeated until the portable imaging device 10 is at or within the target distance range.

Figure 13A:
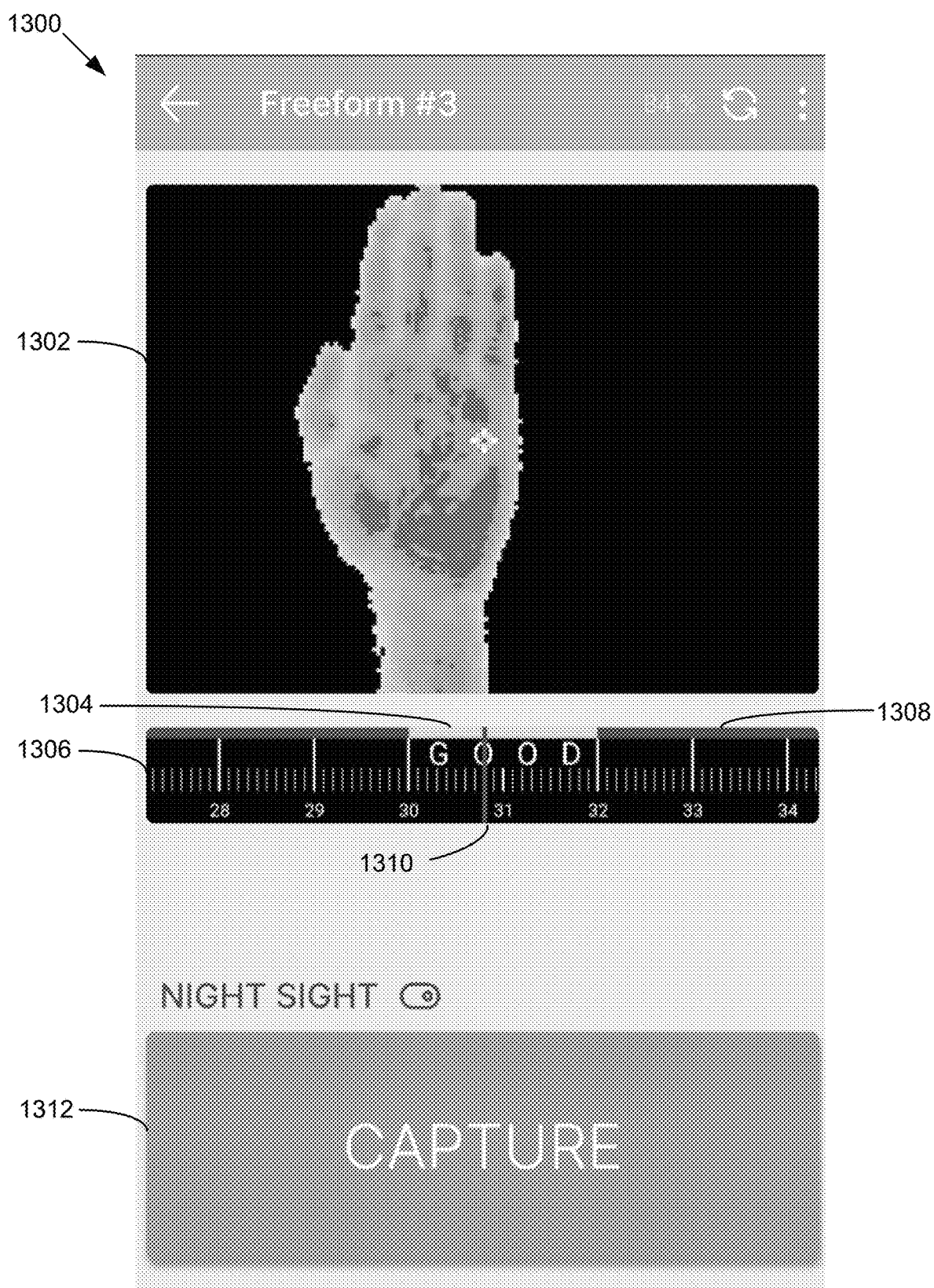
FIG. 13A is a screenshot of an example embodiment of a graphical user interface that may be presented to the user.
Figure 13B:
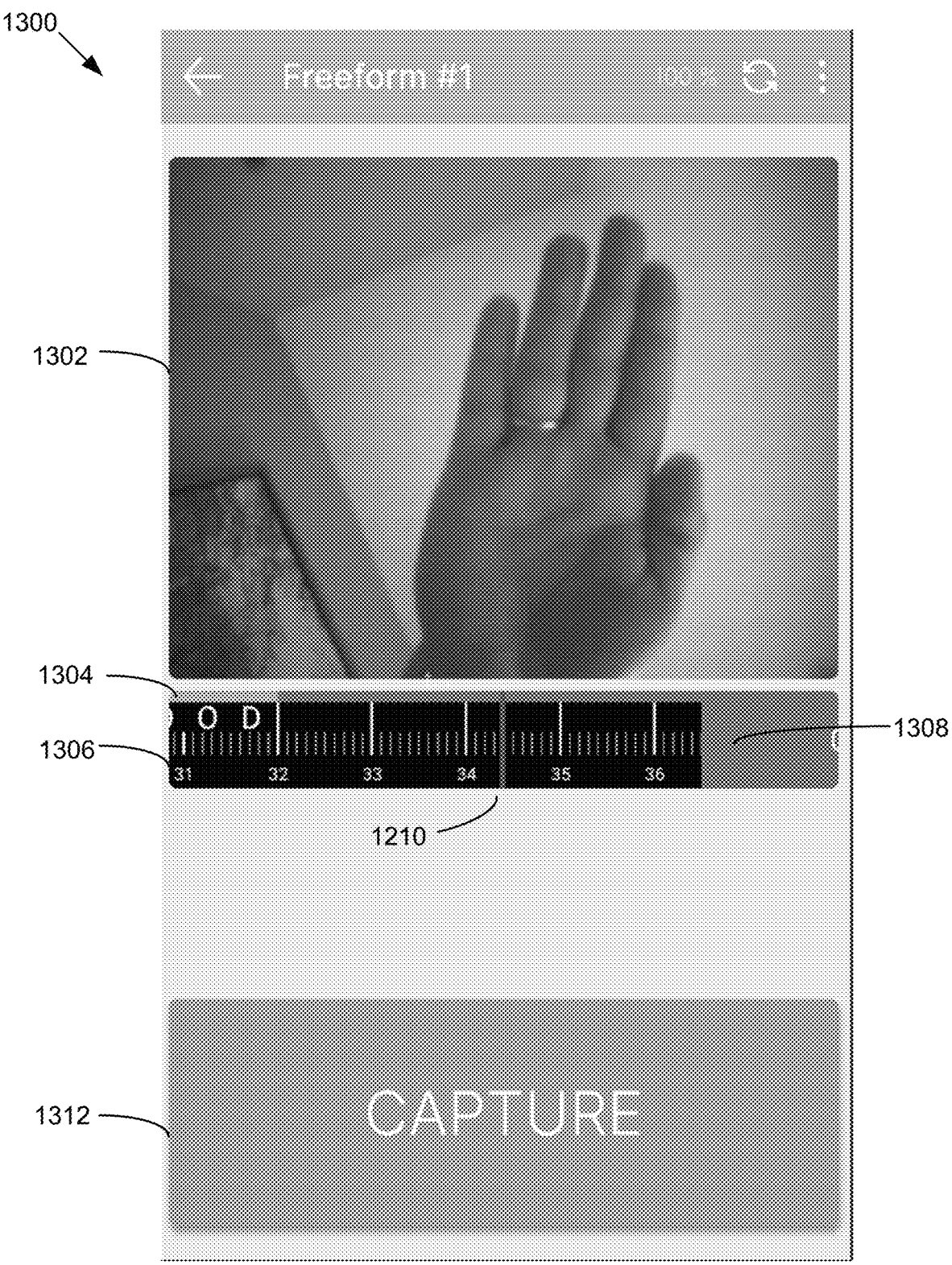
FIG. 13B is another screenshot of an example embodiment of a graphical user interface that may be presented to the user.

Referring simultaneously to FIGS. 13A and 13B, shown therein is a screenshot of an example embodiment of a graphical user interface (GUI) 1300. As shown, the GUI 1300 can include a display 1302 showing a real-time feed of the ROI (FIG. 13B) or a heatmap of the ROI (FIG. 13A) captured by the portable multispectral imaging device 10. The display 1302 may be updated each time a new image frame is captured by the portable multispectral imaging device 10.

GUI 1300 can include tape measure 1306, or other distance indicator, to assist the user in positioning the portable multispectral imaging device 10 and provide feedback. The tape measure can include numerical measurements to further assist the user in correctly positioning the portable multispectral imaging device 10 by visually indicating/displaying if the portable multispectral imaging device 10 is too close or too far from the surface of the ROI. The tape measure 1306 can include a region 1304 indicating that the portable multispectral imagining device 10 is within the target distance range and a region 1308 indicating that the portable multispectral imaging device 10 is not within the target distance range. The regions may be color-coded differently. To indicate the position of the portable multispectral imaging device 10 relative to these two regions, the tape measure 1306 can include a position indicator 1310. When the portable multispectral imaging device 10 is within the target distance range, the position indicator 1310 will be located inside region 1304, as shown in FIG. 13A. When the portable multispectral imaging device 10 is not within an the target distance range, the position indicator 1310 will located inside region 1308 as shown in FIG. 13B. As the portable multispectral imaging device 10 is moved by the user, the position indicator 1310 can move along the tape measure 1306 in real-time or near real-time. Alternatively, the position of the position indicator 1310 may be fixed and the tape measure 1306 may move relative to the position indicator 1310. The position of the tape measure 1306 and/or the position of the position indicator 1310 may be updated at a predetermined frequency and at least as frequently as the display 1302 is updated. The frequency may be determined, for example, based on the type of filter applied to the distance measurements and/or the subject being imaged. For example, when imaging a tissue region of a human subject, since physiological motion in humans generally does not exceed 1 Hz, a low pass filter with a cut off frequency of approximately 2 Hz may be used. In such a case, the maximum rate of update of the position of the tape measure 1306 and/or the position of the position indicator 1310 may be approximately once every 0.5 second. The frequency may also be determined based on the update rate of the display 1302, that is, the tape measure 1306 and/or the position of the position indicator 1310 may be updated each time the display 1302 is refreshed. The frequency can be selected to reduce or eliminate noise from physiological and non-physiological sources.

The GUI 1300 can include a capture button 1312 that can allow the user to capture images. Alternatively, or in addition thereto, the image acquisition module 48 of the portable multispectral imaging device may automatically capture images, for example, once the tissue region (i.e., ROI on the tissue surface) is within the target distance range.

It should be understood that while the various example embodiments in accordance with the teachings herein are described with respect to imaging an ROI on a tissue surface, these embodiments can also be applied to imaging an ROI for any reflective surface and are not limited to being applied to a tissue surface.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without generally departing from the embodiments described herein. For example, while the teachings described and shown herein may comprise certain elements/components and steps, modifications may be made as is known to those skilled in the art. For example, selected features from one or more of the example embodiments described herein in accordance with the teachings herein may be combined to create alternative embodiments that are not explicitly described. All values and sub-ranges within disclosed ranges are also disclosed. The subject matter described herein intends to cover and embrace all suitable changes in technology.

The invention claimed is:

1. A portable multispectral imaging device for imaging a region of interest (ROI) on a surface, wherein the portable imaging device comprises:
    a light sensor for obtaining image datasets of the ROI when the ROI is illuminated;
    a distance sensor for measuring a distance between the portable multispectral imaging device and the ROI of the tissue surface;
    a light source unit comprising an array of LEDs radially disposed around the light sensor for illuminating the ROI of the tissue surface during image capture; and
    an emitter circuit operatively coupled with the light source unit, the emitter circuit comprising a controller circuit having a processor that is operable to:
    determine a change in at least one parameter of the emitter circuit and/or the LEDs causing an actual output light intensity of the array of LEDs to differ from an expected output light intensity, the change in the at least one parameter occurring as the light source unit illuminates the ROI of the tissue surface;
    determine at least one driving intensity correction factor to compensate for the change in the at least one parameter, the at least one driving intensity correction factor being based in part on the measured distance;
    wherein the emitter circuit further comprises:
    a drive circuit configured to generate drive current signals based on the at least one driving intensity correction factor for each of the corresponding at least one LED;
    a multiplexer unit coupled to the drive circuit configured for receiving the drive current signals;
    LED drivers coupled to the drive circuit configured for receiving the drive current signals and controlling a light output intensity for of each of the LEDs;
    wherein the at least one parameter includes temperature, voltage and current, and the processor of the controller circuit is configured to generate the control signals to control the light output intensity of the array of LEDs based on a temperature of the LEDs when the voltage and current provided to the light source unit is held constant, a monitored voltage of the battery unit; and a measured current of the drive circuit;
    and generate control signals for controlling the output light intensity of the array of LEDs, wherein the at least one driving intensity correction factor is applied to the control signal of a corresponding at least one of the LEDs to generate a standardized light intensity output so that a resulting light reflectance from the ROI that is detected by the light sensor is within a range of a desired reflectance intensity.

2. The portable multispectral imaging device of claim 1, wherein the portable multispectral imaging device further comprises:
    a diffusive element that is located to cover the array of LEDs for diffusing light emitted by the array of LEDs, the diffusive element also including an aperture where the light sensor is positioned; and
    a light shield for shielding the light sensor from the light emitted by the array of LEDs.

3. The portable multispectral imaging device of claim 1, wherein the LEDs are radially disposed on a board with an aperture that is aligned with a central axis of the light sensor, and the light shield includes an upper rib for resting on a portion of the board adjacent the aperture in the board and the shield includes a lower housing portion for housing the light sensor.

4. The portable multispectral imaging device of claim 1, the controller circuit is operably coupled to the drive circuit and includes the processor.

5. The portable multispectral imaging device of claim 1, wherein the drive circuit comprises:
    a battery unit having at least one battery;
    a charge level monitor coupled to the battery unit, the charge level monitor being operable to monitor a battery voltage of the battery unit;
    a voltage regulator stage that has at least one voltage regulator and is configured for maintaining the voltage of the battery unit within a desired voltage range;
    a charge management controller that is configured for managing a charge level of the battery unit based on the monitored battery voltage of the battery unit; and
    a current regulator stage for determining the drive current signals.

6. The portable multispectral imaging device of claim 5, wherein the charge management controller is coupled to an external power source for charging the battery unit so that the monitored voltage is within the desired voltage range.

7. The portable multispectral imaging device of claim 1, further comprising a thermistor for measuring the temperature of the array of LEDs, preferably the temperature being a junction temperature.

8. The portable multispectral imaging device of claim 1, wherein the portable multispectral imaging device further comprises a communication unit for communicating with an electronic device.

9. The portable multispectral imaging device of claim 1, further comprising a device processor that is configured to:
   determine whether the measured distance is within a target distance range;
   generate a signal indicating to a user that the portable multispectral imaging device is not within the target distance range and providing instructions to the user to guide that the user for repositioning the portable multispectral imaging device; and
   trigger an image capturing sequence when the portable multispectral imaging device is within the target distance range.

10. The portable multispectral imaging device of claim 1, wherein the processor of the controller circuit is operable to determine the at least one driving intensity correction factor by using a measured value of the at least one parameter as input into a look-up table for each LED, using one or more correction curves or using a polynomial that is defined over an output intensity range for each LED.

\* \* \* \* \*